(12) United States Patent
Kleyman

(10) Patent No.: US 10,912,585 B2
(45) Date of Patent: Feb. 9, 2021

(54) SURGICAL ACCESS DEVICE INCLUDING LATERAL MOVING SEAL COOPERATING WITH BELLOWS ATTACHED TO PROXIMAL WALL OF CANNULA HOUSING

(71) Applicant: Covidien LP, Mansfield, MA (US)

(72) Inventor: Gennady Kleyman, Brooklyn, NY (US)

(73) Assignee: Covidien LP, Mansfield, MA (US)

( * ) Notice: Subject to any disclaimer, the term of this patent is extended or adjusted under 35 U.S.C. 154(b) by 138 days.

(21) Appl. No.: 16/361,328

(22) Filed: Mar. 22, 2019

(65) Prior Publication Data

US 2019/0216501 A1    Jul. 18, 2019

Related U.S. Application Data

(63) Continuation of application No. 15/967,658, filed on May 1, 2018, now Pat. No. 10,238,419, which is a
(Continued)

(51) Int. Cl.
| | |
|---|---|
| *A61B 17/34* | (2006.01) |
| *A61M 39/06* | (2006.01) |
| *A61M 25/06* | (2006.01) |

(52) U.S. Cl.
CPC ...... *A61B 17/3462* (2013.01); *A61B 17/3423* (2013.01); *A61B 17/3474* (2013.01);
(Continued)

(58) Field of Classification Search
CPC ........................ A61B 17/3462; A61B 17/3423
See application file for complete search history.

(56) References Cited

U.S. PATENT DOCUMENTS

| | | |
|---|---|---|
| 5,342,315 A | 8/1994 | Rowe et al. |
| 5,385,553 A | 1/1995 | Hart et al. |

(Continued)

FOREIGN PATENT DOCUMENTS

| | | | |
|---|---|---|---|
| GB | 2287760 A | 9/1995 | |
| GB | 2298905 | * 9/1996 | ......... A61B 17/3462 |
| WO | 9952577 A1 | 10/1999 | |

OTHER PUBLICATIONS

Supplemental Amendment, Sep. 29, 2020 (Year: 2020).*
(Continued)

*Primary Examiner* — Christian A Sevilla
(74) *Attorney, Agent, or Firm* — Carter, DeLuca & Farrell LLP

(57) ABSTRACT

A surgical access device includes a seal assembly having an outer seal housing, an inner seal housing, and a seal cooperating with the inner seal housing, the outer seal housing defining a central longitudinal axis and having a longitudinal passage for receiving at least one surgical object therethrough. The surgical access device also includes a bellows configured to engage at least a portion of the inner seal housing cooperating with the seal, the bellows dimensioned and adapted to establish a biasing relationship with the seal. The seal is adapted for lateral movement relative to the central longitudinal axis of the outer seal housing and the bellows is configured to be attached to a proximal wall of the outer seal housing.

20 Claims, 22 Drawing Sheets

Related U.S. Application Data continuation of application No. 14/768,880, filed as application No. PCT/US2014/017330 on Feb. 20, 2014, now Pat. No. 9,955,998.

(60) Provisional application No. 61/767,363, filed on Feb. 21, 2013.

(52) U.S. Cl.
CPC .. *A61B 2017/3464* (2013.01); *A61M 25/0662* (2013.01); *A61M 39/0606* (2013.01); *A61M 2039/0626* (2013.01); *A61M 2039/0633* (2013.01)

(56) References Cited

U.S. PATENT DOCUMENTS

| | | |
|---|---|---|
| 5,476,475 A | 12/1995 | Gadberry |
| 5,657,963 A | 8/1997 | Hinchliffe et al. |
| 5,827,228 A | 10/1998 | Rowe |
| 5,895,377 A | 4/1999 | Smith et al. |
| 5,989,224 A | 11/1999 | Exline et al. |
| 7,083,626 B2 | 8/2006 | Hart et al. |
| 7,163,525 B2 | 1/2007 | Franer |
| 7,438,702 B2 | 10/2008 | Hart et al. |
| 7,445,625 B2 | 11/2008 | Åkerfeldt |
| 7,785,294 B2 | 8/2010 | Hueil et al. |
| 7,988,671 B2 | 8/2011 | Albrecht et al. |
| 8,007,472 B2 | 8/2011 | Exline et al. |
| 8,206,411 B2 | 6/2012 | Thompson et al. |
| 10,238,419 B2 | 3/2019 | Kleyman |
| 2007/0088277 A1 | 4/2007 | McGinley et al. |
| 2010/0268035 A1 | 10/2010 | Oberlander et al. |
| 2011/0237901 A1 | 9/2011 | Duke et al. |
| 2014/0018631 A1 | 1/2014 | Kleyman |

OTHER PUBLICATIONS

European Office Action dated Oct. 22, 2019, issued in EP Appln. No. 14 754 963.
European Search Report EP14754963 dated Sep. 29, 2016.
European Office Action dated Oct. 13, 2017, issued in EP Appln. No. 14 754 963.

\* cited by examiner

SURGICAL ACCESS DEVICE INCLUDING LATERAL MOVING SEAL COOPERATING WITH BELLOWS ATTACHED TO PROXIMAL WALL OF CANNULA HOUSING

CROSS-REFERENCE TO RELATED APPLICATION

The present application is a continuation of U.S. patent application Ser. No. 15/967,658, filed May 1, 2018, which is a continuation of U.S. patent application Ser. No. 14/768,880, filed Aug. 19, 2015 (now U.S. Pat. No. 9,955,998), which is a National Stage Application of PCT/US2014/017330 under 35 USC § 371 (a), filed Feb. 20, 2014, which claims the benefit of and priority to Provisional Application Ser. No. 61/767,363, filed Feb. 21, 2013, the disclosure of which is incorporated by reference herein in its entirety.

BACKGROUND

Technical Field

The present disclosure relates to a seal system adapted to permit the introduction of surgical instrumentation into a patient's body. In particular, the present disclosure relates to a seal system for use with an introducer or access device, which is intended for insertion into a patient's body, and to receive an instrument in sealing engagement therewith.

Background of Related Art

Minimally invasive and laparoscopic procedures generally require that any instrumentation inserted into the body is sealed, i.e., provisions must be made to ensure that gases and/or fluids do not enter or exit the body through an endoscopic incision, such as, for example in surgical procedures where the surgical region is insufflated. For such procedures, the introduction of a tube into anatomical cavities, such as the peritoneal cavity, is usually accomplished by use of a system incorporating a trocar and cannula assembly. Since the cannula is in direct communication with the interior of the peritoneal cavity, insertion of the cannula into an opening in the patient's body to reach the inner abdominal cavity should be adapted to maintain a fluid tight interface between the abdominal cavity and the outside atmosphere.

In view of the need to maintain the atmospheric integrity of the inner area of the cavity, a seal assembly for a cannula, which permits introduction of a wide range of surgical instrumentation and maintains the atmospheric integrity of the inner area of the cavity, is desirable. In this regard, there have been a number of attempts in the prior art to achieve such sealing requirements. A difficulty encountered with conventional seal assemblies, however, is the inability of accommodating the wide range of sizes of instrumentation. In addition, angulation and/or manipulation of instrumentation within the cannula often present difficulties with respect to maintaining seal integrity.

SUMMARY

According to one aspect of the present disclosure, a surgical access device is provided. The surgical access device includes a seal assembly including an outer seal housing, an inner seal housing, and a seal cooperating with the inner seal housing, the outer seal housing defining a central longitudinal axis and having a longitudinal passage for receiving at least one surgical object therethrough and a bellows configured to engage at least a portion of the inner seal housing cooperating with the seal, the bellows dimensioned and adapted to establish a biasing relationship with the seal. The seal is adapted for lateral movement relative to the central longitudinal axis of the outer seal housing and the bellows is configured to be attached to a proximal wall of the outer seal housing.

In one exemplary embodiment, the bellows causes friction between the seal and the inner seal housing to be overcome to permit the seal to align with the central longitudinal axis of the outer seal housing.

In yet another exemplary embodiment, the bellows is circumferentially adjacent the longitudinal passage of the outer seal housing.

In another exemplary embodiment, the outer seal housing defines an angular opening therethrough to facilitate angular reception of the at least one surgical object.

Additionally, the bellows is dimensioned and adapted to inhibit passage of fluids through the outer seal housing.

In one exemplary embodiment, the bellows enables self-centering of the seal after the at least one surgical object has been removed from the longitudinal passage.

In another exemplary embodiment, the bellows extends to a proximal wall of the outer seal housing in parallel to the central longitudinal axis defined by the outer seal housing.

In yet another exemplary embodiment, the bellows is positioned within a space such that the seal is movable relative to the outer seal housing, the space defined between the outer seal housing and the inner seal housing.

In yet another exemplary embodiment, one side of the bellows expands and another side of the bellows contracts as the at least one surgical object in inserted through and maneuvered within the longitudinal passage of the outer seal housing.

In an alternative embodiment, the bellows connects to the seal to form a single integral unit.

In another aspect of the present disclosure, a cannula assembly is provided. The cannula assembly includes a cannula housing, a cannula sleeve extending distally from the cannula housing and a seal assembly disposed in mechanical cooperation with the cannula housing. The seal assembly includes a seal assembly including an outer seal housing, an inner seal housing, and a seal cooperating with the inner seal housing, the outer seal housing defining a central longitudinal axis and having a longitudinal passage for receiving at least one surgical object therethrough and a bellows configured to engage at least a portion of the inner seal housing cooperating with the seal, the bellows dimensioned and adapted to establish a biasing relationship with the seal. The seal is adapted for lateral movement relative to the central longitudinal axis of the outer seal housing and the bellows is configured to be attached to a proximal wall of the outer seal housing.

Further scope of applicability of the present disclosure will become apparent from the detailed description given hereinafter. However, it should be understood that the detailed description and specific examples, while indicating preferred embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

Figure 1:
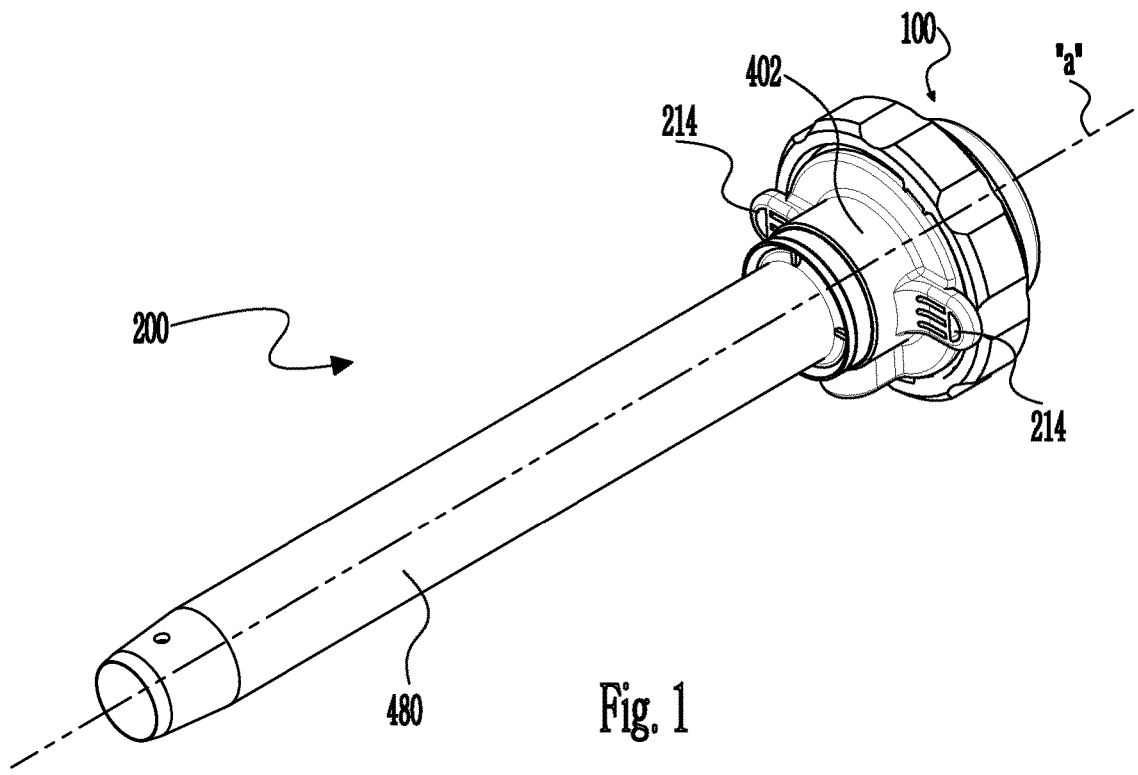
FIGS. 1-2 are perspective views of a cannula assembly and a seal assembly.

The figures depict preferred embodiments of the present disclosure for purposes of illustration only. One skilled in the art will readily recognize from the following discussion that alternative embodiments of the structures and methods illustrated herein may be employed without departing from the principles of the present disclosure described herein.

DETAILED DESCRIPTION

Particular embodiments of the present disclosure are described hereinbelow with reference to the accompanying drawings. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

For the purposes of promoting an understanding of the principles of the present disclosure, reference will now be made to the exemplary embodiments illustrated in the drawings, and specific language will be used to describe the same. It will nevertheless be understood that no limitation of the scope of the present disclosure is thereby intended. Any alterations and further modifications of the inventive features illustrated herein, and any additional applications of the principles of the present disclosure as illustrated herein, which would occur to one skilled in the relevant art and having possession of this disclosure, are to be considered within the scope of the present disclosure.

The seal assembly of the present disclosure, either alone or in combination with a seal system internal to a cannula assembly, provides a substantial seal between a body cavity of a patient and the outside atmosphere before, during and after insertion of an instrument through the cannula assembly. Moreover, the seal assembly of the present invention is capable of accommodating instruments of varying diameters, e.g., from 5 mm to 15 mm, by providing a gas tight seal with each instrument when inserted. The flexibility of the present seal assembly greatly facilitates endoscopic surgery where a variety of instruments having differing diameters are often needed during a single surgical procedure.

The seal assembly contemplates the introduction and manipulation of various types of instrumentation adapted for insertion through a trocar and/or cannula assembly while maintaining a fluid tight interface about the instrumentation to preserve the atmospheric integrity of a surgical procedure from gas and/or fluid leakage. Specifically, the seal assembly accommodates angular manipulation of the surgical instrument relative to the seal housing axis. This feature of the present disclosure desirably minimizes the entry and exit of gases and/or fluids to/from the body cavity. Examples of instrumentation include clip appliers, graspers, dissectors, retractors, staplers, laser probes, photographic devices, endoscopes and laparoscopes, tubes, and the like. Such instruments will be collectively referred to herein as "instruments or instrumentation."

Embodiments of the presently disclosed apparatus will now be described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Figure 2:
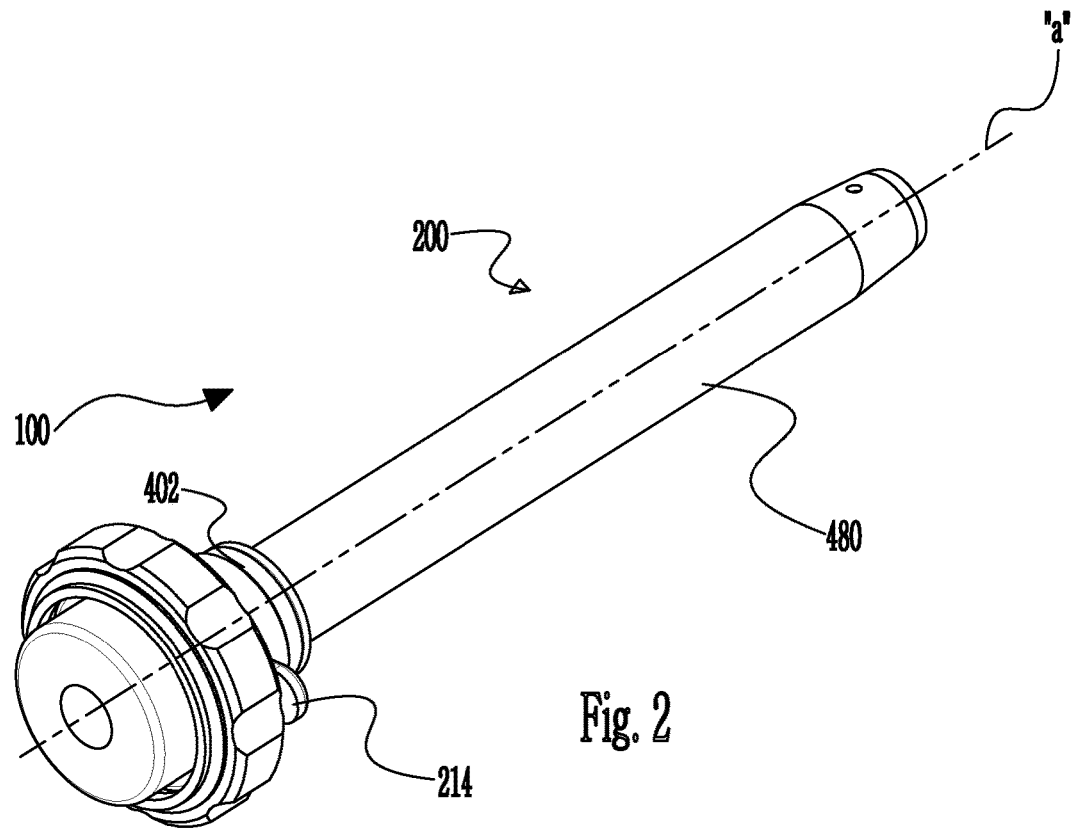

Referring now to the drawings, in which like reference numerals identify identical or substantially similar parts throughout the several views, FIGS. 1-2 illustrate the seal assembly 100 of the present disclosure mounted to cannula assembly 200. Cannula assembly 200 may be any conventional cannula suitable for the intended purpose of accessing a body cavity and permit introduction of instruments therethrough. Cannula assembly 200 is particularly adapted for use in laparoscopic surgery where the peritoneal cavity is insufflated with a suitable gas, e.g., $CO_2$, to raise the cavity wall from the internal organs therein. Cannula assembly 200 is typically used with an obturator assembly (not shown), which is a sharp pointed instrument positionable within the passageway of the cannula assembly 200. The obturator assembly is utilized to penetrate the abdominal wall and then subsequently be removed from the cannula assembly to permit introduction of the surgical instrumentation utilized to perform the procedure.

Cannula assembly 200 includes cannula sleeve 480 and cannula housing 402 mounted to an end of the sleeve 480. Cannula sleeve 480 defines a longitudinal axis "a" extending along the length of sleeve 480. Sleeve 480 further defines an internal longitudinal passage dimensioned to permit passage of surgical instrumentation. Sleeve 480 may be formed of stainless steel or other rigid materials, such as a polymeric material or the like. Sleeve 480 may be clear or opaque. The diameter of sleeve 480 may vary, but typically ranges from 10 to 15 mm for use with the seal assembly 100 of the present disclosure. Cannula housing 402 further includes diametrically opposed housing grips 214 dimensioned and arranged for gripping engagement by the fingers of the user.

Figure 3:
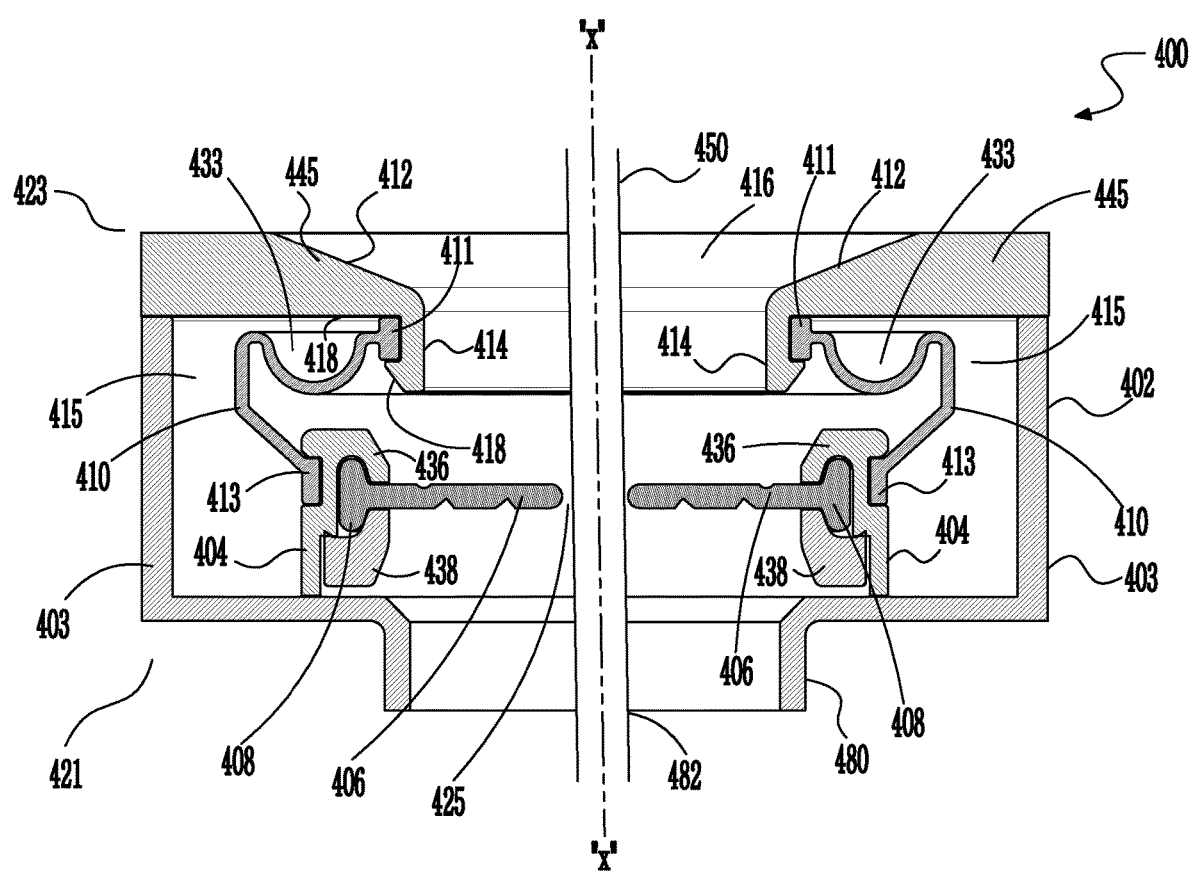
FIG. 3 is a side cross-sectional view of the cannula assembly including a flat seal cooperating with an inner seal housing, in accordance with an embodiment of the present disclosure.

Referring to FIG. 3, a side cross-sectional view 400 of the seal assembly 100 including a flat seal 406 cooperating with an inner seal housing 404, in accordance with an embodiment of the present disclosure is presented.

Cannula housing 402 is adapted and dimensioned to include an inner seal housing 404 therein. Inner seal housing 404 includes a first housing component 436 and a second housing component 438 configured to matingly engage each other to form the inner seal housing 404. Inner seal housing 404 is configured to accommodate seal 406, which is a flat seal. Seal 406 is mounted in a manner that permits lateral movement of the seal 406 relative to seal axis "x." Seal 406 includes a connecting member 408, at an outer edge portion, adapted and dimensioned to be received between the first housing component 436 and the second housing component 438. The inner seal housing 404 enables the seal 406 to be in a flat configuration by securing or stabilizing the connecting member 408 between the first housing component 436 and the second housing component 438. The connecting member 408 has a thickness greater than the thickness of the seal 406. Seal 406 also includes an aperture 425 centrally disposed therethrough for receiving surgical instrument 450, as will be described below.

It is noted that the top portion of the cannula housing 402 includes angled portions 412 for enabling angular insertion of the surgical instrument 450. The angulation allows for easier insertion and manipulation of the surgical instrument 450. The angled portions 412 taper off to define an inner guide wall 414. The inner guide wall 414 may be a substantially vertical wall that is parallel to axis "x." An outer wall 418 is defined within a proximal end of annular space 415. Annular space 415 includes a bellows 410 having a proximal end 411 (or first end) and a distal end 413 (or second end). The bellows 410 is confined within the annular space 415. A portion of the outer wall 418 is configured to receive and secure the proximal end 411 of bellows 410. The distal end 413 of the bellows 410 is configured to be received and secured by the first housing component 436. The first housing component 436 may include a recess for receiving the distal end 413 of bellows 410. The bellows 410 acts as a centering unit for maintaining the seal 406 in a stretched and/or compressed position when the surgical instrument 450 is inserted through opening 416. It is contemplated that the centering unit 410 is some type of flexible or semi-rigid rubber structure. In FIG. 3, the bellows 410 is shown in an un-tensioned or neutral configuration 433. In other words, insertion of the surgical instrument 450 does not cause deflection or displacement of the bellows 410.

As illustrated, the first end 411 of the bellows 410 is attached or connected to a proximal wall 445 of the cannula housing 402. The second end 413 of the bellows 410 seals the outer part of the seal 406 to inhibit leakage, thus eliminating the need for an interface seal. Thus, bellows 410 provides some self-centering that pushes or readjusts the seal 406 toward a centered, neutral position. Therefore, the first end 411 of the bellows 410 connects to a top wall or top portion or top segment or distal portion/segment of the cannula housing 402 (as opposed to the side walls 403 of the cannula housing 402). The vertical structure of the bellows 410 also provides self-centering that pushes the seal 406 toward a center position with respect to axis "x." Moreover, the width (and overall size of the system) of the cannula housing 402 may be reduced by constructing the bellows 410 as a vertical structure that connects to the top wall of the cannula housing 402 because less space is required on the sides of the cannula housing 402. Thus, the space between the side walls 403 of the cannula housing 402 and the outer surface of the inner seal housing 404 need not be adapted and dimensioned to accommodate the size of the bellows 410, as the bellows 410 extends adjacent the outer surface of the inner seal housing 404, vertically toward the top wall of the cannula housing 402. In other words, the radial width of the cannula housing 402 may be decreased substantially.

In operation, the instrument 450 passes into the cannula housing 402 passing through opening 416 and cannula sleeve 480 into the body cavity. In other words, the instrument 450 moves from the proximal end 423 toward the distal end 421 of the surgical access system 400. Once the instrument 450 is disposed within aperture 425, seal 406 moves laterally with respect to the cannula housing 402, as the instrument 450 is manipulated (described in detail with reference to FIGS. 4 and 5). The distal end of the surgical instrument 450 exits through opening 482 of sleeve 480 to access a body cavity of a patient to perform one or more surgical procedures.

Figure 4:
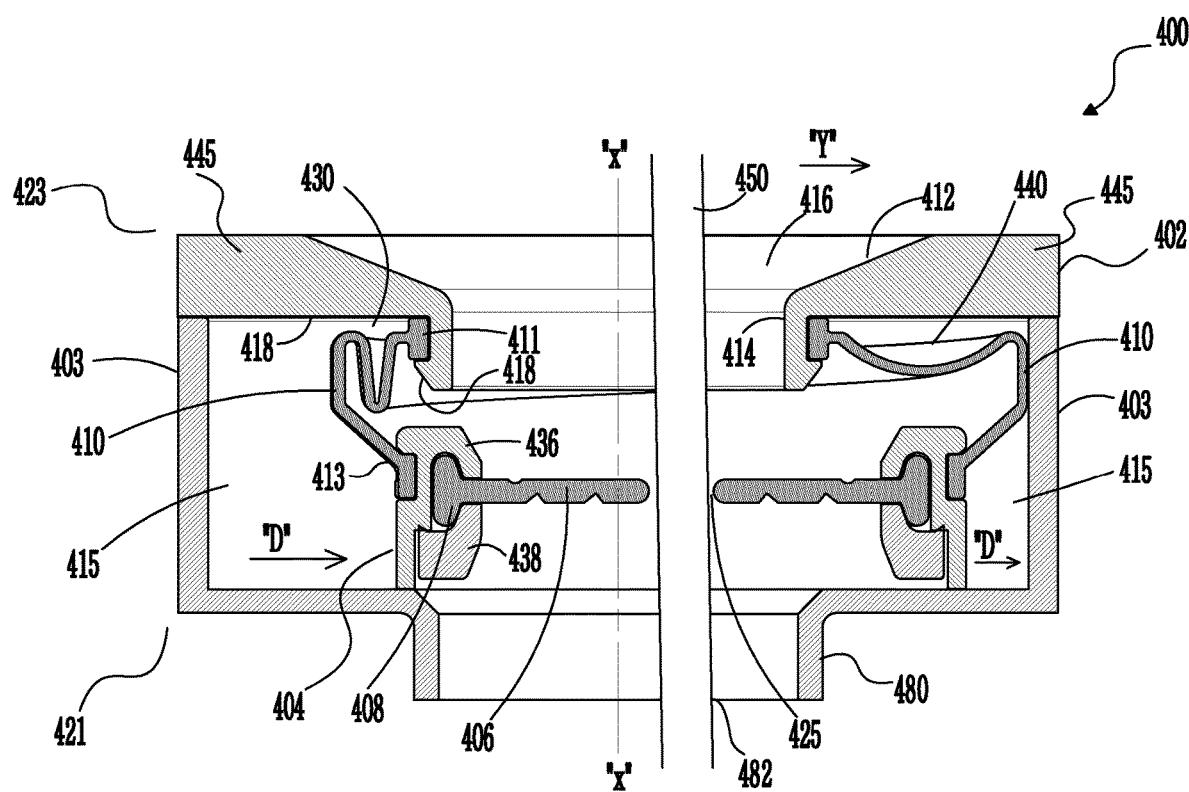
FIG. 4 is a side cross-sectional view of the flat seal of FIG. 3 moved to the right as a surgical object is inserted through the longitudinal passage of the cannula housing, in accordance with an embodiment of the present disclosure.
Figure 5:
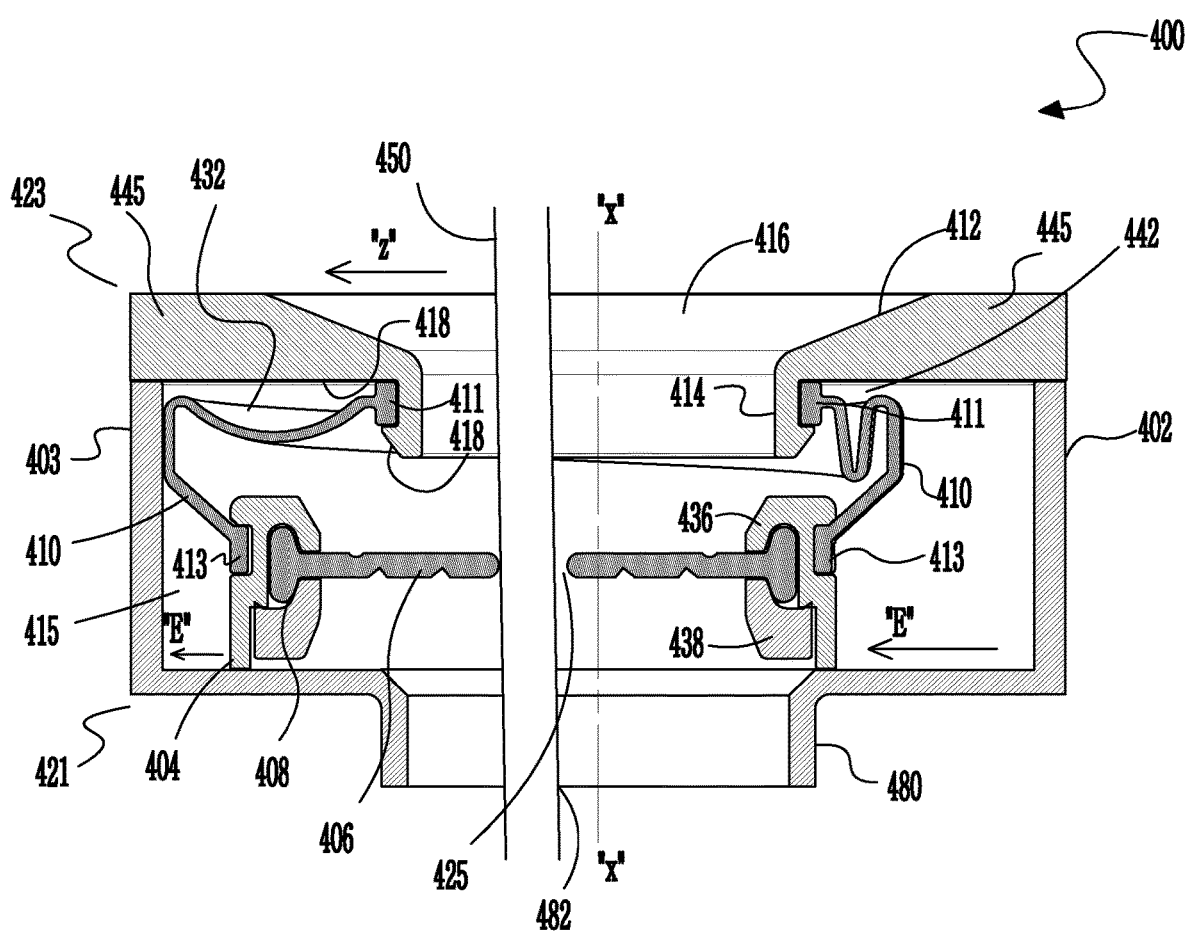
FIG. 5 is a side cross-sectional view of the flat seal of FIG. 3 moved to the left as a surgical object is inserted through the longitudinal passage of the cannula housing, in accordance with an embodiment of the present disclosure.

Referring to FIG. 4, a side cross-sectional view 400 of the flat seal 406 moved to the right as the surgical instrument 450 is inserted through the longitudinal passage 416 of the cannula housing 402 is presented, whereas FIG. 5 is a side cross-sectional view 400 of the flat seal 406 moved to the left as the surgical instrument 450 is inserted through the longitudinal passage 416 of the cannula housing 402, in accordance with an embodiment of the present disclosure.

As shown in FIG. 4, seal 406 has been moved in a direction "D." For example, the surgical instrument 450 is inserted through opening 416 of the cannula housing 402 to move the seal 406 to the right. Surgical instrument 450 has moved in direction "y" to cause such displacement or deflection of the bellows 410. As shown in FIG. 5, seal 406 has been moved in a direction "E." For example, the surgical instrument 450 is inserted through opening 416 of the cannula housing 402 to move the seal 406 to the left. Surgical instrument 450 has moved in direction "z" to cause such displacement or deflection of the bellows 410. In FIG. 4, it is noted that the left side of the bellows 410 is in a compressed configuration 430, whereas the right side of the bellows 410 is in a stretched configuration 440 due to movement of the surgical instrument 450 to the right of axis "x". In FIG. 5, it is noted that the right side of the bellows 410 is in a compressed configuration 442, whereas the right side of the bellows 410 is in a stretched configuration 432 due to movement of the surgical instrument 450 to the left of axis "x". Therefore, insertion of the surgical instrument 450 through aperture 425 causes the entire inner seal housing 404 to slidably or frictionally engage the bottom portion of the cannula housing 402 and move from one side wall 403 toward the other side wall 403. The side-to-side movement or displacement of the inner seal housing 404 in turn causes the bellows 410 to expand and contract based on corresponding movement of the surgical instrument 450. It is contemplated that the bellows 410 expands and contracts within the entire annular space 415, such that the bellows 410 may extend all the way to the side walls 403 of the cannula housing 402. When instrument 450 is removed, bellows 410 returns to a neutral state by expanding the compressed side and contracting the expanded side.

After the surgical instrument 450 has been removed from the cannula housing 402, bellows 410 enables seal 406 to move back to its original position (i.e., a neutral central position, shown in FIG. 3). The un-tensioned position is one where the seal 406 is centered with respect to axis "x." Stated differently, bellows 410 may force or propel or guide seal 406 to return to a position co-axial with the cannula housing 402. Thus, displacement of seal 406 from a substantially central position is negated by bellows 410, once the surgical instrument 450 has been removed. Bellows 410 may be moved or adjusted or displaced within the annular space 415 in order to re-position the seal 406 to a substantially central position with respect to the cannula housing 402. Moreover, the distal end 413 of the bellows 410 is configured to aid the movement of the seal 406 since the distal end 413 of the bellows 410 is attached to the first housing component 436 of the inner seal housing 404.

In summary, bellows 410 is attached or connected or secured to a proximal wall 445 (or distal end or distal portion/segment or top wall) of the cannula housing 402, thus enabling the bellows 410 to freely move within the annular space 415 without any hindrances from any other components. As a result, this configuration seals the outward part of the seal 406 to the cannula housing 402 to inhibit leakage.

Figure 6:
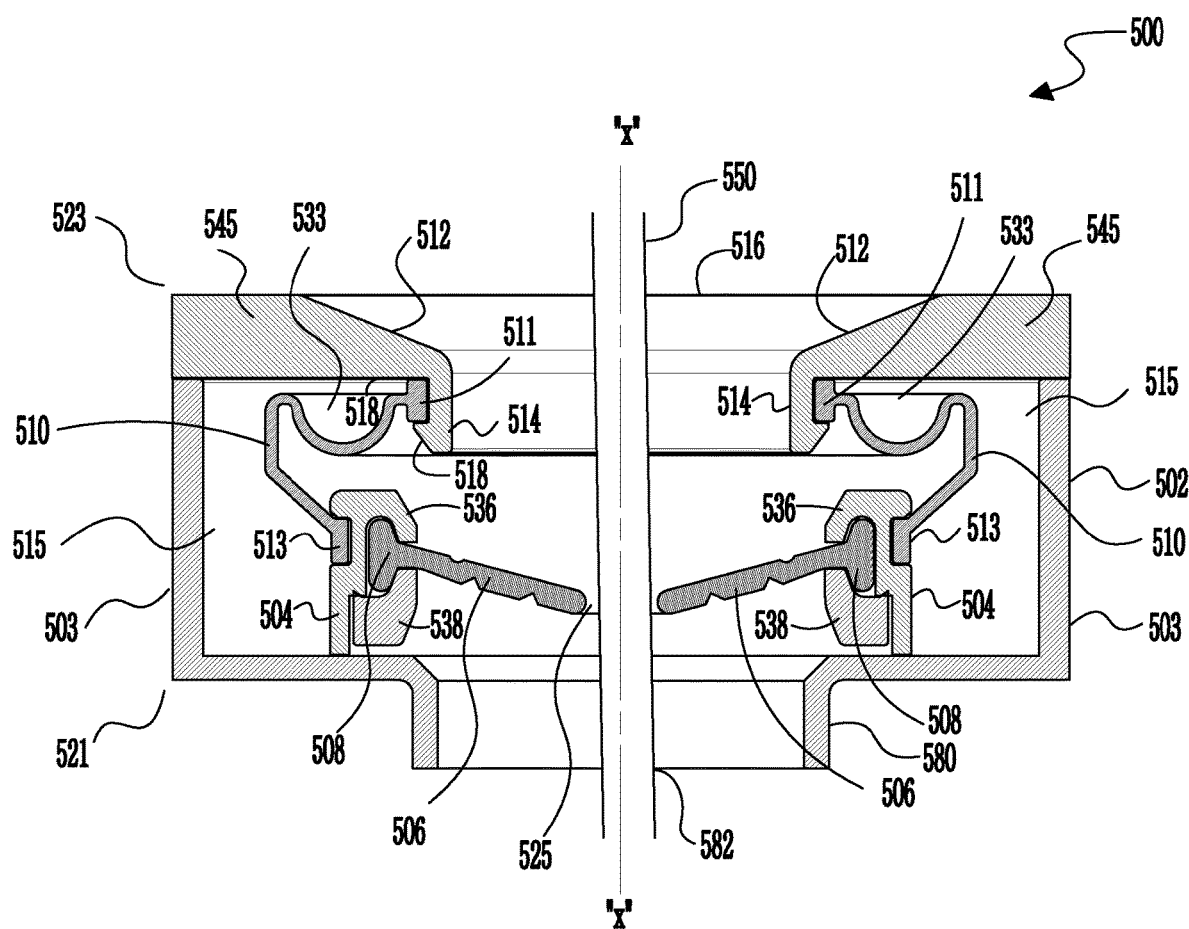
FIG. 6 is a side cross-sectional view of a cannula assembly including a seal cooperating with an inner seal housing, the seal being slightly conical, in accordance with another embodiment of the present disclosure.

Referring to FIG. 6, a side cross-sectional view 500 of a seal assembly 100 including a seal 506 cooperating with an inner seal housing 504 is presented, where the seal 506 is slightly conical in accordance with another embodiment of the present disclosure.

Cannula housing 502 is adapted and dimensioned to include an inner seal housing 504 therein. Inner seal housing 504 includes a first housing component 536 and a second housing component 538 configured to matingly engage each other to form the inner seal housing 504. Inner seal housing 504 is configured to accommodate seal 506, which is a slightly conical seal. Seal 506 is mounted in a manner that permits lateral movement of the seal 506 relative to seal axis "x." Seal 506 includes a connecting member 508, at a distal end thereof, adapted and dimensioned to be received between the first housing component 536 and the second housing component 538. The inner seal housing 504 enables the seal 506 to be in a slightly conical configuration by securing or stabilizing the connecting member 508 between the first housing component 536 and the second housing component 538. The connecting member 508 has a thickness greater than the thickness of the seal 506. Seal 506 also includes an aperture 525 centrally disposed therethrough for receiving surgical instrument 550. Slightly conical refers to the seal 506 having a distal end that is tapered downward. Stated differently, the seal 506 may be slightly frusto-conical in nature.

It is noted that the top portion of the cannula housing 502 includes angled portions 512 for enabling angular insertion of the surgical instrument 550. The angulation allows for easier insertion and manipulation of the surgical instrument 550. The angled portions 512 taper off to define an inner guide wall 514. The inner guide wall 514 may be a substantially vertical wall that is parallel to axis "x." An outer wall 518 is defined within a proximal end of annular space 515. Annular space 515 includes a bellows 510 having a proximal end 511 (or first end) and a distal end 513 (or second end). The bellows 510 is confined within the annular space 515. A portion of the outer wall 518 is configured to receive and secure the proximal end 511 of bellows 510. The distal end 513 of the bellows 510 is configured to be received and secured by the first housing component 536. The first housing component 536 may include a recess for receiving the distal end 513 of bellows 510. The bellows 510 acts as a centering unit for maintaining the seal 506 in a compressed or tensioned position when the surgical instrument 550 is inserted through opening 516. It is contemplated that the centering unit 510 is some type of flexible or semi-rigid rubber structure. In FIG. 6, the bellows 510 is shown in an un-tensioned or neutral configuration 533. In other words, insertion of the surgical instrument 550 does not cause deflection or displacement of the bellows 510.

As illustrated, the first end 511 of the bellows 510 is attached or connected to a proximal wall 545 of the cannula housing 502. The second end 513 of the bellows 510 seals the outer part of the seal 506 to inhibit leakage, thus eliminating the need for an interface seal. Thus, bellows 510 provides some self-centering that pushes or readjusts the seal 506 toward a centered, un-tensioned position. Therefore, the first end 511 of the bellows 510 connects to a top wall or top portion or top segment or distal portion/segment of the cannula housing 502 (as opposed to the side walls 503 of the cannula housing 502). The vertical structure of the bellows 510 also provides self-centering that pushes the seal 506 toward a center position with respect to axis "x." Moreover, the width (and overall size of the system) of the cannula housing 502 may be reduced by constructing the bellows 510 as a vertical structure that connects to the top wall of the cannula housing 502 because less space is required on the sides of the cannula housing 502. Thus, the space between the side walls 503 of the cannula housing 502 and the outer surface of the inner seal housing 504 need not be adapted and dimensioned to accommodate the size of the bellows 510, as the bellows 510 extends adjacent the outer surface of the inner seal housing 504, vertically toward the top wall of the cannula housing 502. In other words, the radial width of the cannula housing 502 may be decreased substantially.

In operation, the instrument 550 passes into the cannula housing 502 passing through opening 516 and cannula sleeve 580 into the body cavity. In other words, the instrument 550 moves from the proximal end 523 toward the distal end 521 of the surgical access system 500. Once the instrument 550 is disposed within aperture 525, seal 506 moves laterally with respect to the cannula housing 502, as the instrument 550 is manipulated (described in detail with reference to FIGS. 7 and 8). The distal end of the surgical instrument 550 exits through opening 582 of sleeve 580 to access a body cavity of a patient to perform one or more surgical procedures.

Figure 7:
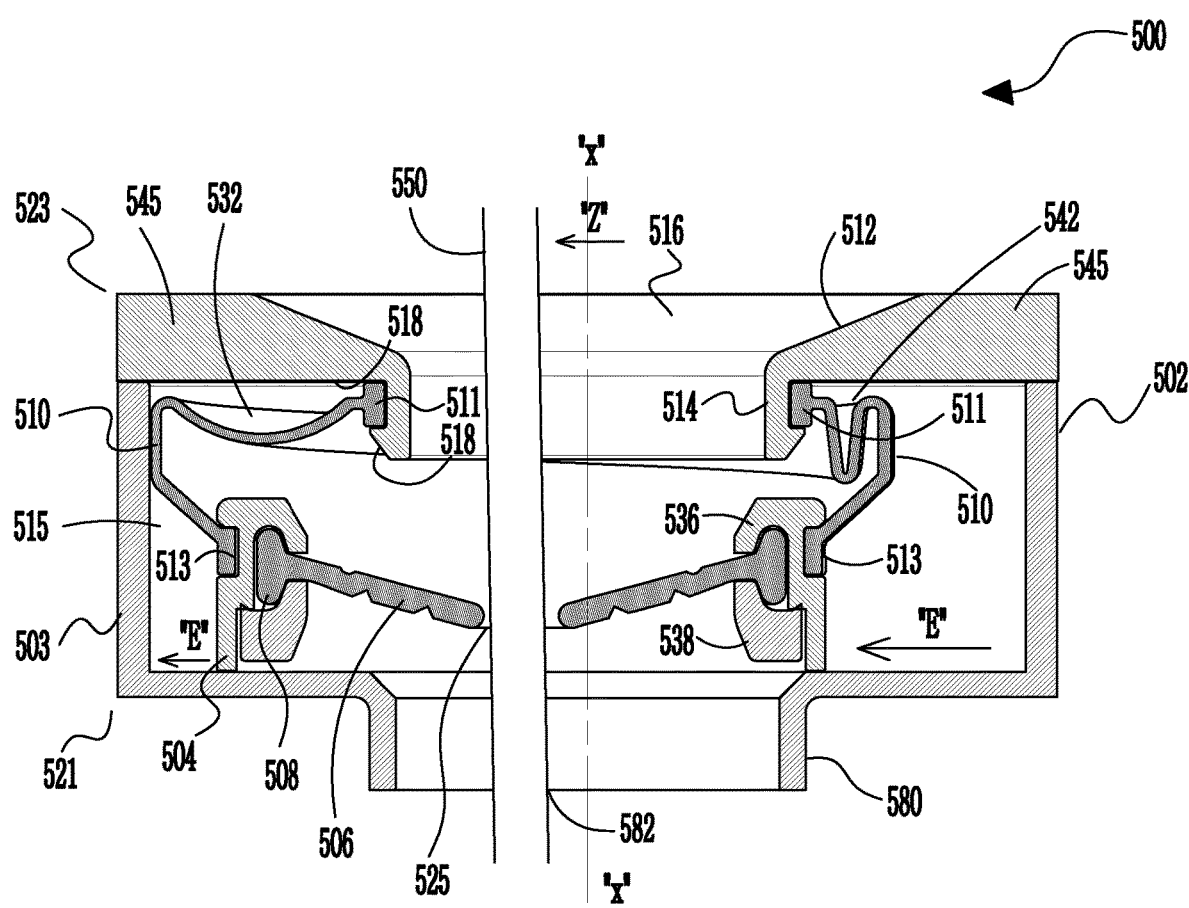
FIG. 7 is a side cross-sectional view of the slightly conical seal of FIG. 6 moved to the left as a surgical object is inserted through the longitudinal passage of the cannula housing, in accordance with an embodiment of the present disclosure.
Figure 8:
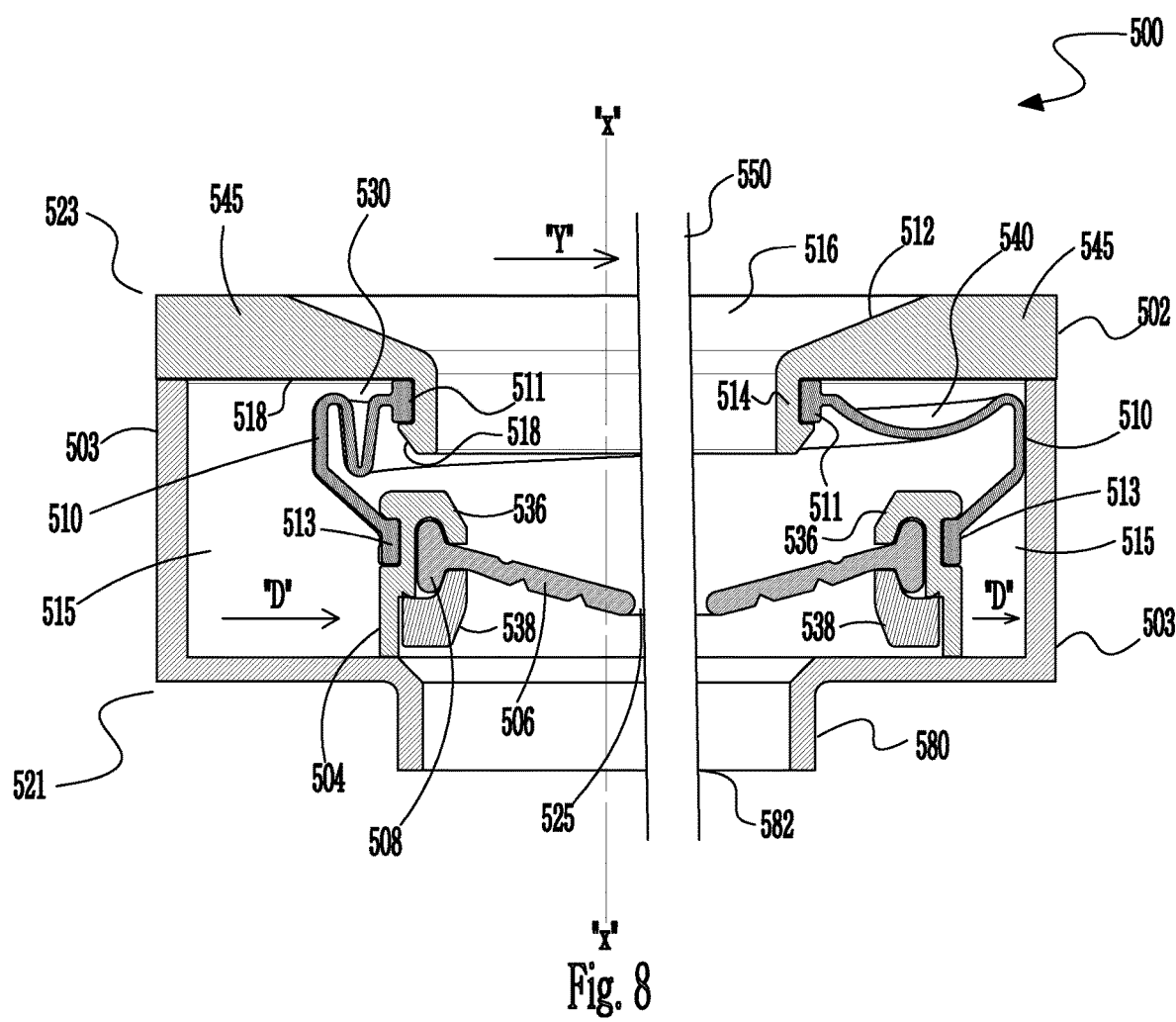
FIG. 8 is a side cross-sectional view of the slightly conical seal of FIG. 6 moved to the right as a surgical object is inserted through the longitudinal passage of the cannula housing, in accordance with an embodiment of the present disclosure.

Referring to FIG. 7, a side cross-sectional view 500 of the slightly conical seal 506 moved to the left as the surgical instrument 550 is inserted through the longitudinal passage 516 of the cannula housing 502 is presented, whereas FIG. 8 is a side cross-sectional view 500 of the slightly conical seal 506 moved to the right as the surgical instrument 550 is inserted through the longitudinal passage 516 of the cannula housing 502, in accordance with another embodiment of the present disclosure.

As shown in FIG. 7, seal 506 has been moved in a direction "E." For example, the surgical instrument 550 is inserted through opening 516 of the cannula housing 502 to move the seal 506 to the left. Surgical instrument 550 has moved in direction "z" to cause such displacement or deflection of the bellows 510. As shown in FIG. 8, seal 506 has been moved in a direction "D." For example, the surgical instrument 550 is inserted through opening 516 of the cannula housing 502 to move the seal 506 to the right. Surgical instrument 550 has moved in direction "y" to cause such displacement or deflection of the bellows 510. In FIG. 7, it is noted that the right side of the bellows 510 is in a compressed configuration 542, whereas the left side of the bellows 510 is in a stretched configuration 532 due to movement of the surgical instrument 550 to the left of axis "x". In FIG. 8, it is noted that the left side of the bellows 510 is in a compressed configuration 530, whereas the right side of the bellows 510 is in a stretched configuration 540 due to movement of the surgical instrument 550 to the right of axis "x". Therefore, insertion of the surgical instrument 550 through aperture 525 causes the entire inner seal housing 504 to slidably or frictionally engage the bottom portion of the cannula housing 502 and move from one side wall 503 toward the other side wall 503. The side-to-side movement or displacement of the inner seal housing 504 in turn causes the bellows 510 to expand and contract based on corresponding movement of the surgical instrument 550. It is contemplated that the bellows 510 expands and contracts within the entire annular space 515, such that the bellows 510 may extend all the way to the side walls 503 of the cannula housing 502. When instrument 550 is removed, bellows 510 returns to a neutral state by expanding the compressed side and contracting the expanded side.

After the surgical instrument 550 has been removed from the cannula housing 502, bellows 510 enables seal 506 to move back to its original position (i.e., an un-tensioned position, shown in FIG. 6). The un-tensioned or neutral position is one where the seal 506 is centered with respect to axis "x." Stated differently, bellows 510 may force or propel or guide seal 506 to return to a position co-axial with the cannula housing 502. Thus, displacement of seal 506 from a substantially central position is negated by bellows 510, once the surgical instrument 550 has been removed. Bellows 510 may be moved or adjusted or displaced within the annular space 515 in order to re-position the seal 506 to a substantially central position with respect to the cannula housing 502. Moreover, the distal end 513 of the bellows 510 is configured to aid the movement of the seal 506 since the distal end 513 of the bellows 510 is attached to the first housing component 536 of the inner seal housing 504.

In summary, bellows 510 is attached or connected or secured to a proximal wall 545 (or distal end or distal portion/segment or top wall) of the cannula housing 502, thus enabling the bellows 510 to freely move within the annular space 515 without any hindrances from any other components. As a result, this configuration seals the outward part of the seal 506 to the cannula housing 502 to inhibit leakage.

Figure 9:
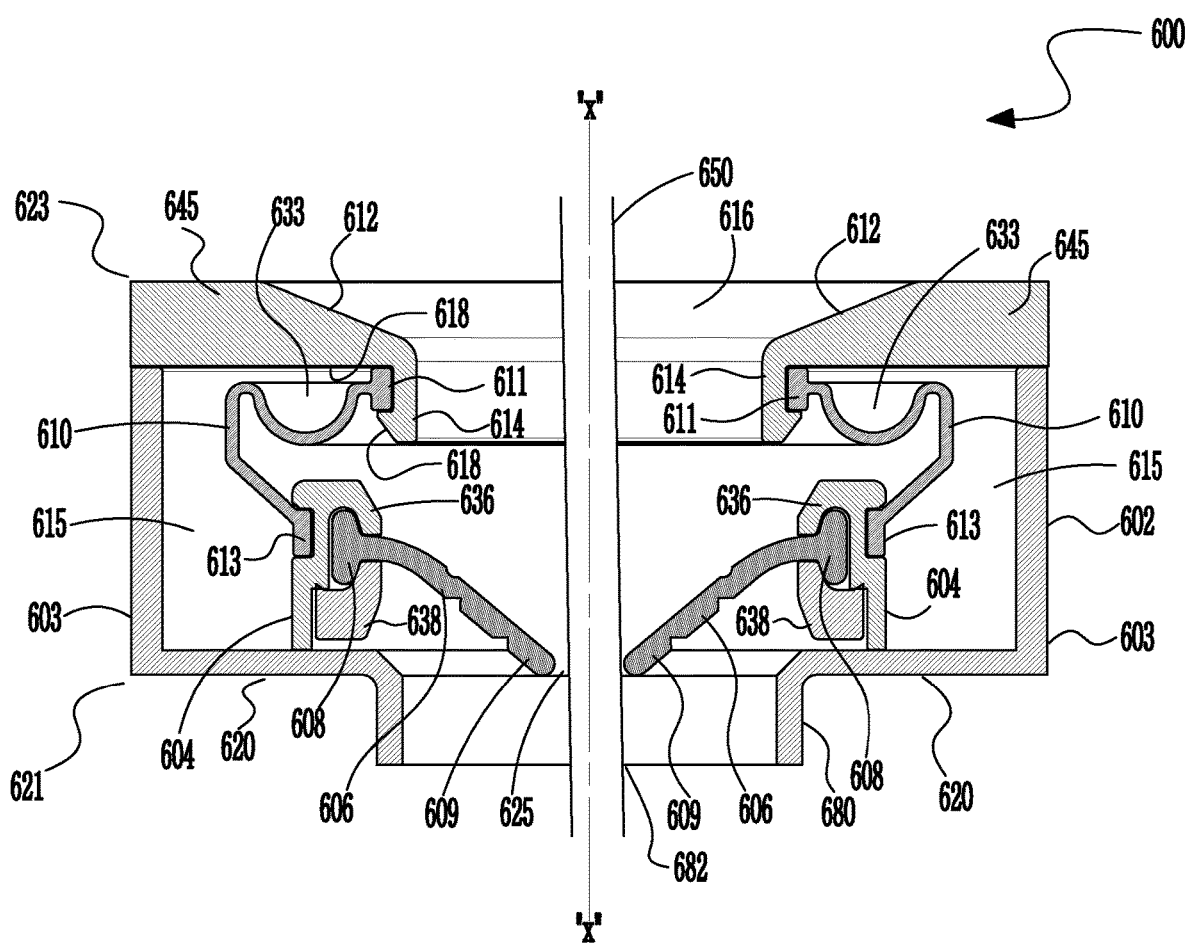
FIG. 9 is a side cross-sectional view of the seal assembly including a seal cooperating with an inner seal housing, the seal being of a steep conical configuration, in accordance with another embodiment of the present disclosure.

Referring to FIG. 9, a side cross-sectional view 600 of a seal assembly 100 including a seal 606 cooperating with an inner seal housing 604 is presented, where the seal 606 is a steeply conical in accordance with another embodiment of the present disclosure.

Cannula housing 602 is adapted and dimensioned to include an inner seal housing 604 therein. Inner seal housing 604 includes a first housing component 636 and a second housing component 638 configured to matingly engage each other to form the inner seal housing 604. Inner seal housing 604 is configured to accommodate seal 606, which is a steeply conical seal. Seal 606 is mounted in a manner that permits lateral movement of the seal 606 relative to seal axis "x." Seal 606 includes a connecting member 608, at a distal end thereof, adapted and dimensioned to be received between the first housing component 636 and the second housing component 638. The inner seal housing 604 enables the seal 606 to be in a steeply conical configuration by securing the connecting member 608 between the first housing component 636 and the second housing component 638. The connecting member 608 has a thickness greater than the thickness of the seal 606. Seal 606 also includes an aperture 625 centrally disposed therethrough for receiving surgical instrument 650. Steeply conical refers to the seal 606 having a distal end that is tapered downward (at an angle greater than the angle for the slightly conical configuration of FIGS. 6-8). Stated differently, the seal 606 may be steeply frusto-conical in nature.

It is noted that the top portion of the cannula housing 602 includes angled portions 612 for enabling angular insertion of the surgical instrument 650. The angulation allows for easier insertion and manipulation of the surgical instrument 650. The angled portions 612 taper off to define an inner guide wall 614. The inner guide wall 614 may be a substantially vertical wall that is parallel to axis "x." An outer wall 618 is defined within a proximal end of annular space 615. Annular space 615 includes a bellows 610 having a proximal end 611 (or first end) and a distal end 613 (or second end). The bellows 610 is confined within the annular space 615. A portion of the outer wall 618 is configured to receive and secure the proximal end 611 of bellows 610. The distal end 613 of the bellows 610 is configured to be received and secured by the first housing component 636. The first housing component 636 may include a recess for receiving the distal end 613 of bellows 610. The bellows 610 acts as a centering unit for maintaining the seal 606 in a compressed or tensioned position when the surgical instrument 650 is inserted through opening 616. It is contemplated that the centering unit 610 is some type of flexible or semi-rigid rubber structure. In FIG. 9, the bellows 610 is shown in an un-tensioned or neutral configuration 633. In other words, insertion of the surgical instrument 650 does not cause deflection or displacement of the bellows 610.

As illustrated, the first end 611 of the bellows 610 is attached or connected to a proximal wall 645 of the cannula housing 602. The second end 613 of the bellows 610 seals the outer part of the seal 606 to inhibit leakage, thus eliminating the need for an interface seal. Thus, bellows 610 provides some self-centering that pushes or readjusts the seal 606 toward a centered, un-tensioned position. Therefore, the first end 611 of the bellows 610 connects to a top wall or top portion or top segment or distal portion/segment of the cannula housing 602 (as opposed to the side walls 603 of the cannula housing 602). The vertical structure of the bellows 610 also provides self-centering that pushes the seal 606 toward a center position with respect to axis "x." Moreover, the width (and overall size of the system) of the cannula housing 602 may be reduced by constructing the bellows 610 as a vertical structure that connects to the top wall of the cannula housing 602 because less space is required on the sides of the cannula housing 602. Thus, the space between the side walls 603 of the cannula housing 602 and the outer surface of the inner seal housing 604 need not be adapted and dimensioned to accommodate the size of the bellows 610, as the bellows 610 extends adjacent the outer surface of the inner seal housing 604, vertically toward the top wall of the cannula housing 602. In other words, the radial width of the cannula housing 602 may be decreased substantially.

In operation, the instrument 650 passes into the cannula housing 602 passing through opening 616 and cannula sleeve 680 into the body cavity. In other words, the instrument 650 moves from the proximal end 623 toward the distal end 621 of the surgical access system 600. Once the instrument 650 is disposed within aperture 625, seal 606 moves laterally with respect to the cannula housing 602, as the instrument 650 is manipulated (described in detail with reference to FIGS. 10 and 11). The distal end of the surgical instrument 650 exits through opening 682 of sleeve 680 to access a body cavity of a patient to perform one or more surgical procedures.

Figure 10:
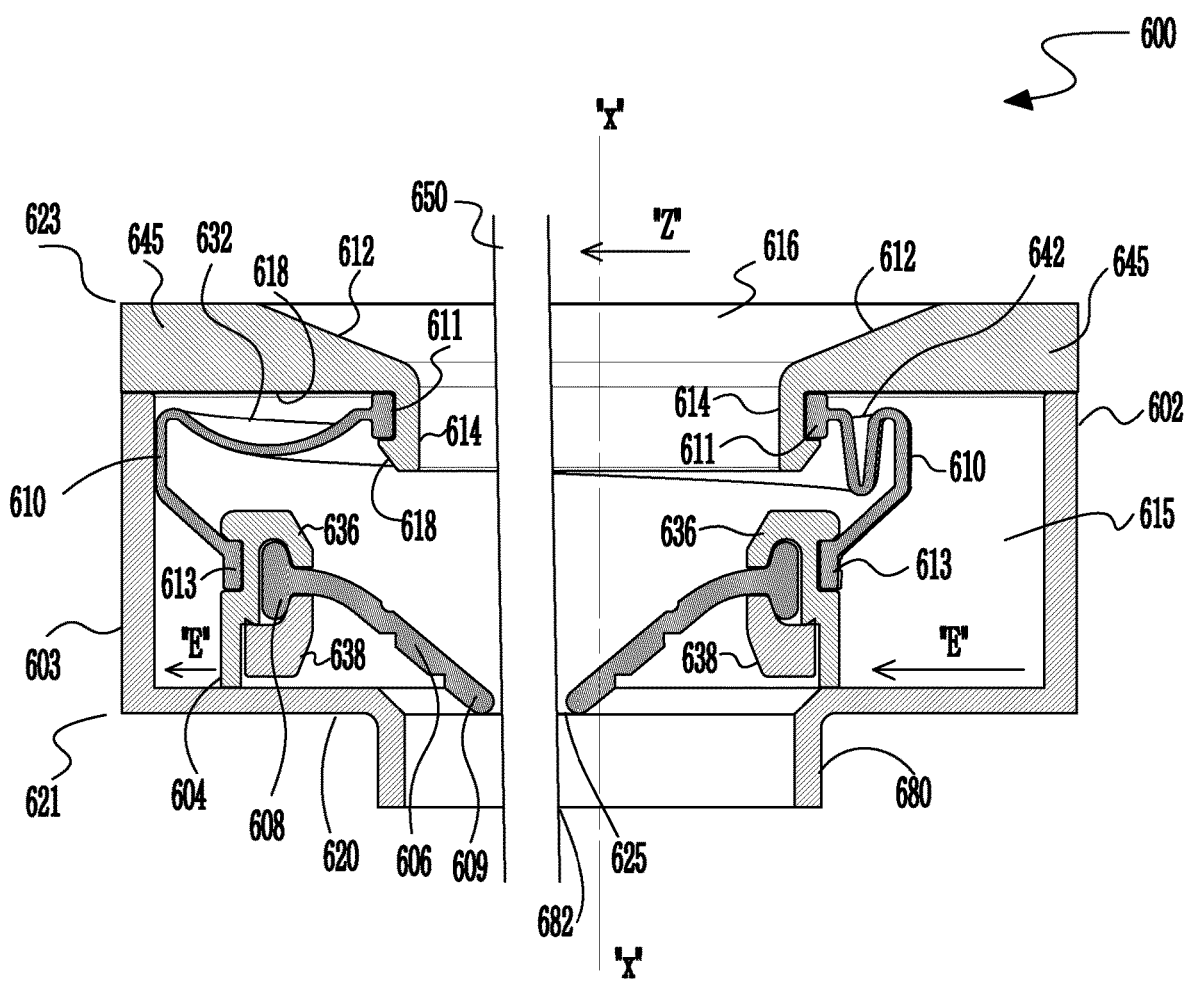
FIG. 10 is a side cross-sectional view of the steep conical seal of FIG. 9 moved to the left as a surgical object is inserted through the longitudinal passage of the cannula housing, in accordance with an embodiment of the present disclosure.
Figure 11:
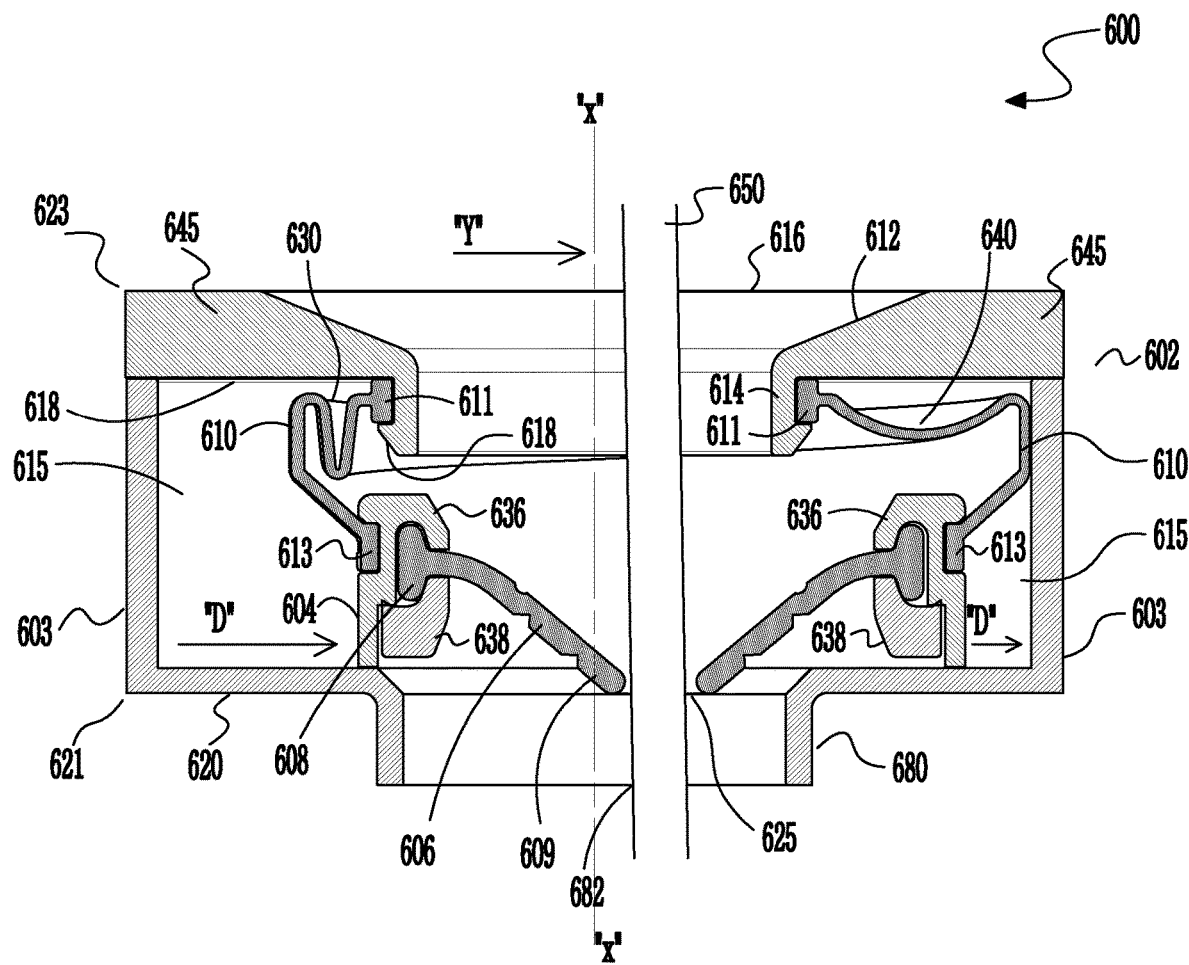
FIG. 11 is a side cross-sectional view of the steep conical seal of FIG. 9 moved to the right as a surgical object is inserted through the longitudinal passage of the cannula housing, in accordance with an embodiment of the present disclosure.

Referring to FIG. 10, a side cross-sectional view 600 of the steeply conical seal 606 moved to the left as the surgical instrument 650 is inserted through the longitudinal passage 616 of the cannula housing 602 is presented, whereas FIG. 11 is a side cross-sectional view 600 of the steeply conical seal 606 moved to the right as the surgical instrument 650 is inserted through the longitudinal passage 616 of the cannula housing 602, in accordance with another embodiment of the present disclosure.

As shown in FIG. 10, seal 606 has been moved in a direction "E." For example, the surgical instrument 650 is inserted through opening 616 of the cannula housing 602 to move the seal 606 to the left. Surgical instrument 650 has moved in direction "z" to cause such displacement or deflection of the bellows 610. As shown in FIG. 11, seal 606 has been moved in a direction "D." For example, the surgical instrument 650 is inserted through opening 616 of the cannula housing 602 to move the seal 606 to the right. Surgical instrument 650 has moved in direction "y" to cause such displacement or deflection of the bellows 610. In FIG. 10, it is noted that the right side of the bellows 610 is in a compressed configuration 642, whereas the left side of the bellows 610 is in a stretched configuration 632 due to movement of the surgical instrument 650 to the left of axis "x". In FIG. 11, it is noted that the left side of the bellows 610 is in a compressed configuration 630, whereas the right side of the bellows 610 is in a stretched configuration 640 due to movement of the surgical instrument 650 to the right of axis "x". Therefore, insertion of the surgical instrument 650 through aperture 625 causes the entire inner seal housing 604 to slidably or frictionally engage the bottom portion of the cannula housing 602 and move from one side wall 603 toward the other side wall 603. The side-to-side movement or displacement of the inner seal housing 604 in turn causes the bellows 610 to expand and contract based on corresponding movement of the surgical instrument 650. It is contemplated that the bellows 610 expands and contracts within the entire annular space 615, such that the bellows 610 may extend all the way to the side walls 603 of the cannula housing 602.

After the surgical instrument 650 has been removed from the cannula housing 602, bellows 610 enables seal 606 to move back to its original position (i.e., an un-tensioned or neutral position, shown in FIG. 9). The un-tensioned position is one where the seal 606 is centered with respect to axis "x." Stated differently, bellows 610 may force or propel or guide seal 606 to return to a position co-axial with the cannula housing 602. Thus, displacement of seal 606 from a substantially central position is negated by bellows 610, once the surgical instrument 650 has been removed. Bellows 610 may be moved or adjusted or displaced within the annular space 615 in order to re-position the seal 606 to a substantially central position with respect to the cannula housing 602. Moreover, the distal end 613 of the bellows 610 is configured to aid the movement of the seal 606 since the distal end 613 of the bellows 610 is attached to the first housing component 636 of the inner seal housing 604.

In summary, bellows 610 is attached or connected or secured to a proximal wall 645 (or distal end or distal portion/segment or top wall) of the cannula housing 602, thus enabling the bellows 610 to freely move within the annular space 615 without any hindrances from any other components. As a result, this configuration seals the outward part of the seal 606 to the cannula housing 602 to inhibit leakage.

Figure 12A:
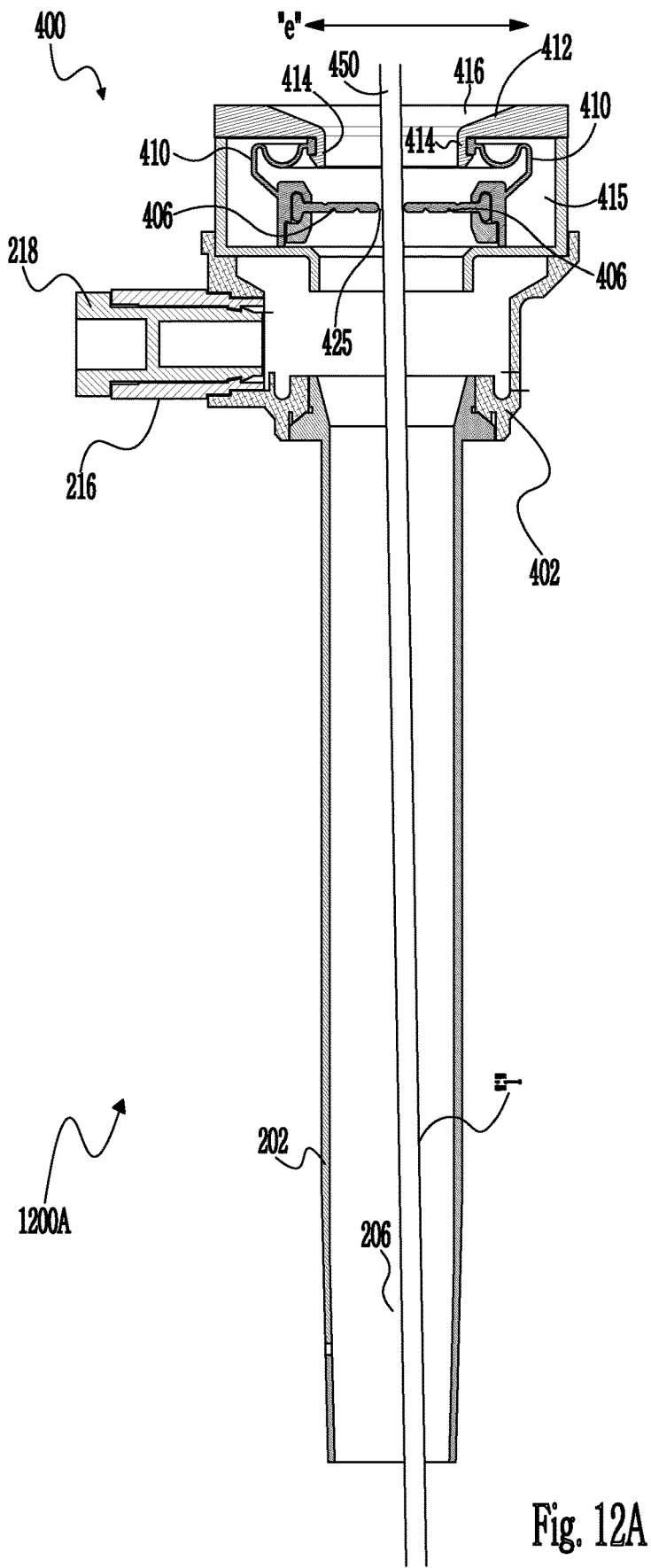
FIGS. 12A-12C, are side cross-sectional views of the cannula and seal assemblies illustrating a range of movement of the surgical instrument inserted through the flat, slightly conical, and steep conical seals, respectively, where the instrument moves to expand/contract the bellows, in accordance with the embodiments of the present disclosure.
Figure 12B:
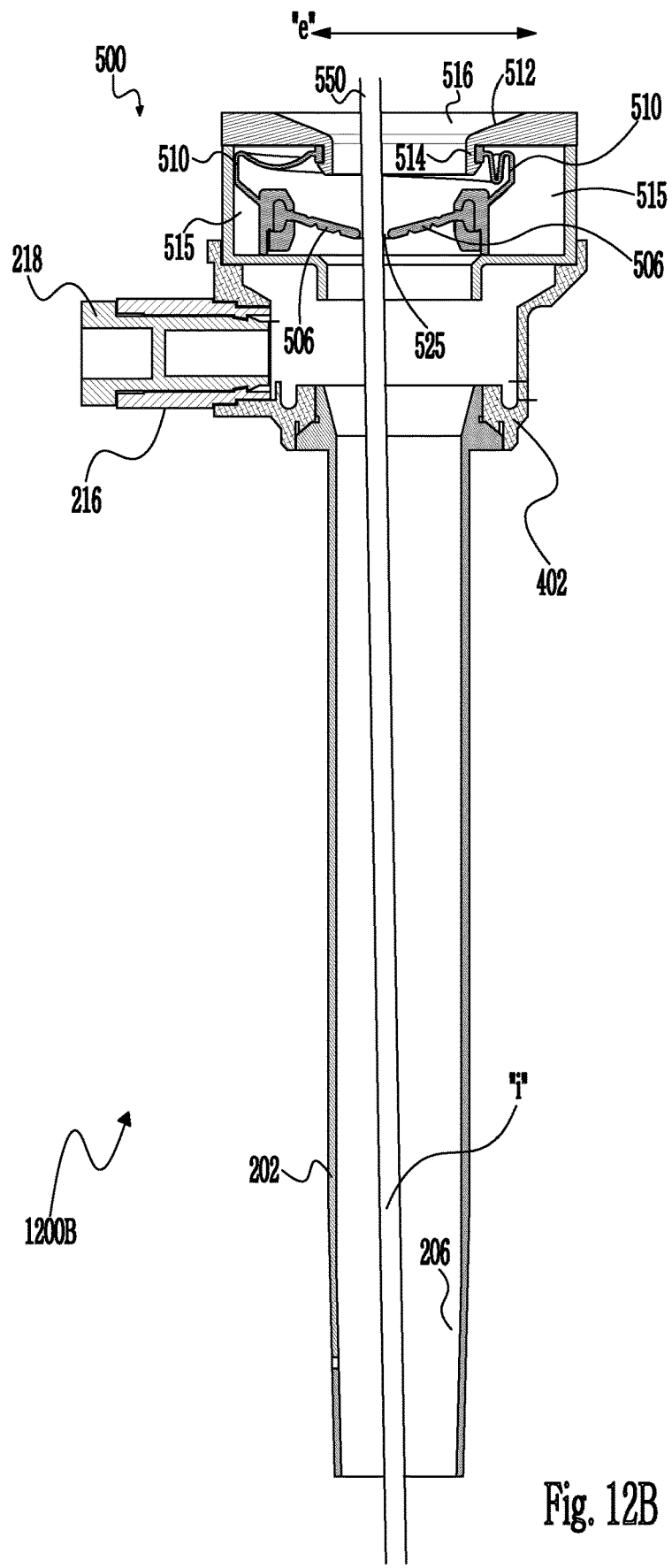
Figure 12C:
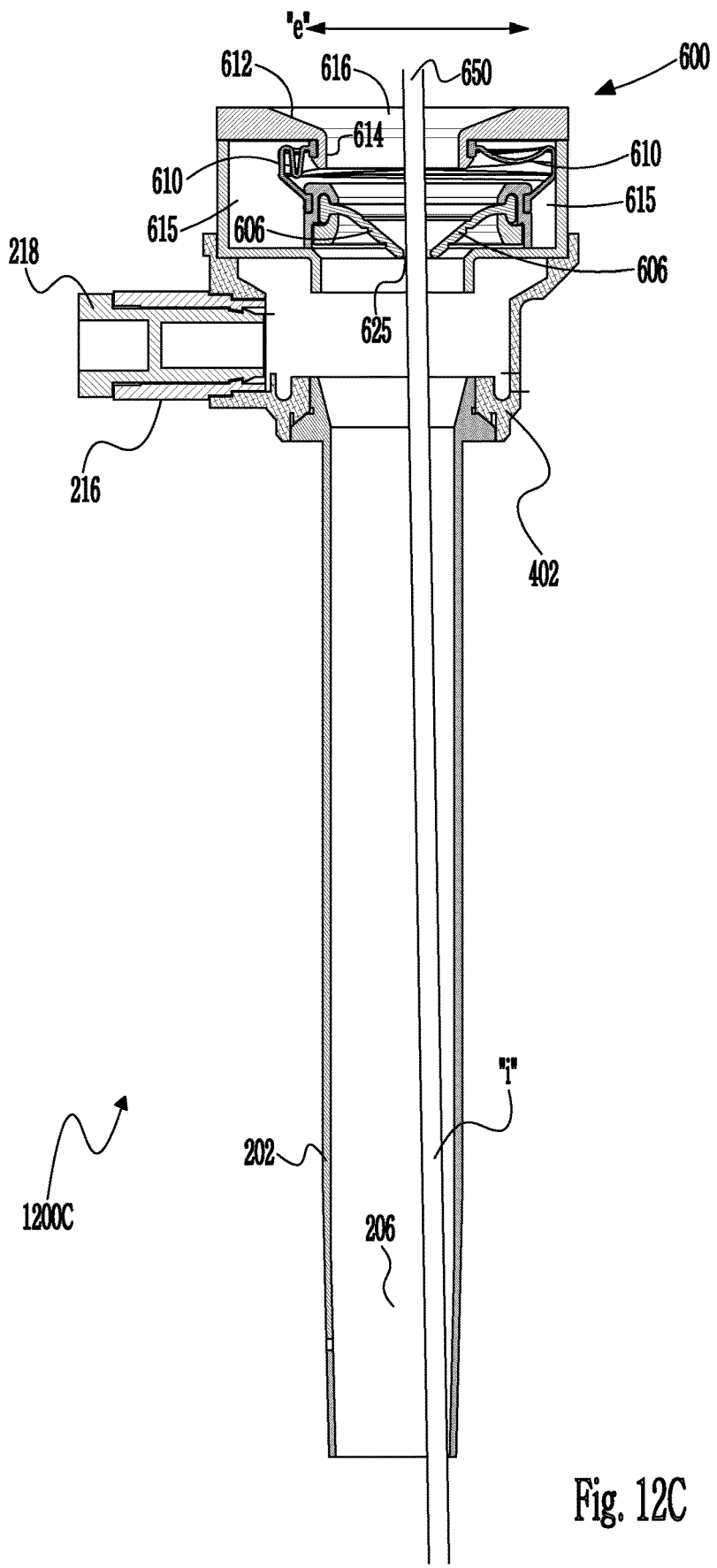

FIGS. 12A-12C illustrate side cross-sectional views 1200A-1200C of the instrument "i" inserted through the seal assembly 100 connected to the cannula assembly 200.

FIG. 12A illustrates the flat seal 406, FIG. 12B illustrates the slightly conical seal 506, and FIG. 12C illustrates the steeply conical seal 606. For example, referring to FIG. 12A, seal assembly 100 is mounted to cannula assembly 200, which was previously introduced into an insufflated abdominal cavity. An instrument "i" is inserted into seal assembly 100 through passage 416. Cannula housing 402 may include a port opening and luer fitting 216 positioned within the port opening. Luer fitting 216 is adapted for connection to a supply of insufflation gas and incorporates valve 218 to selectively open and close the passage of the luer fitting 216. If the axis of the instrument "i" is not perfectly aligned with the axis "a" of cannula assembly 200, then the surgical instrument contacts the inner guide wall 414. Contact with the seal 406 may cause displacement of the seal 406 either to the left or to the right, since the seal 406 is a laterally moving seal. The instrument "i" slides through aperture 425 of seal 406, which stretches to accommodate the instrument diameter, as necessary. A similar process is shown for FIGS. 12B and 12C, which relate to the slightly conical seal 506 and the steeply conical seal 606.

In operation or use, as the instrument "i" is moved up and down axis "e," bellows 410, 510, 610 maintain the instrument "i" in its tensioned position, as desired by the user. The biased position is an off-center positioned with respect to axis "x," as illustrated in FIGS. 3-11. When the instrument "i" is removed from the seal assembly 100 and cannula assembly 200, bellows 410, 510, 610 re-positions the seal 406, 506, 606, respectively, back to their centered and un-tensioned or neutral positions. The un-tensioned position is a substantially central position with respect to axis "x." Thus, bellows 410, 510, 610 act to negate the displacement caused by the insertion of one or more surgical instruments through the cannula assembly 100 and the seal assembly 200.

Figure 13A:
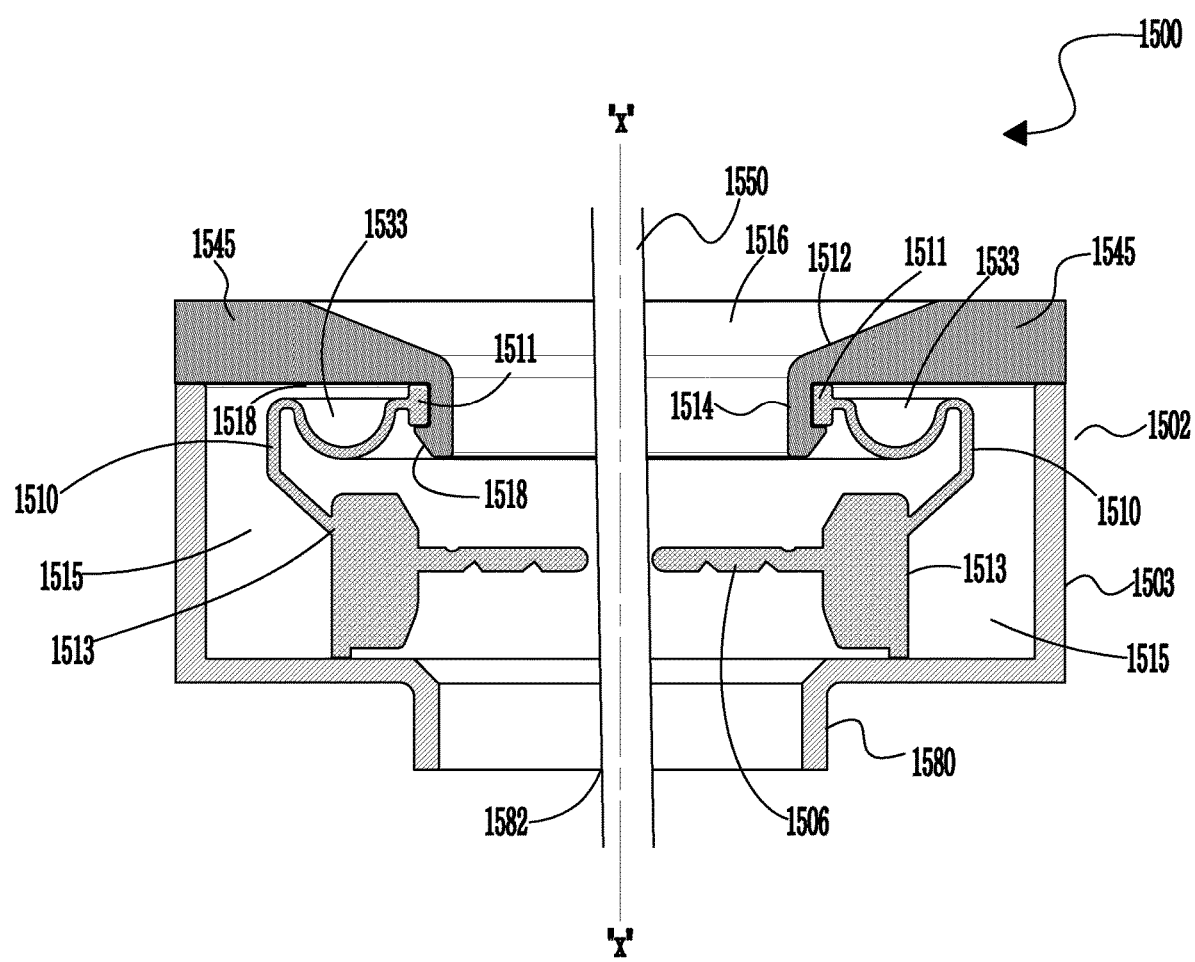
FIG. 13A is a side view of a flat seal, where the bellows and the flat seal are one integral unit, in accordance with another embodiment of the present disclosure.
Figure 13B:
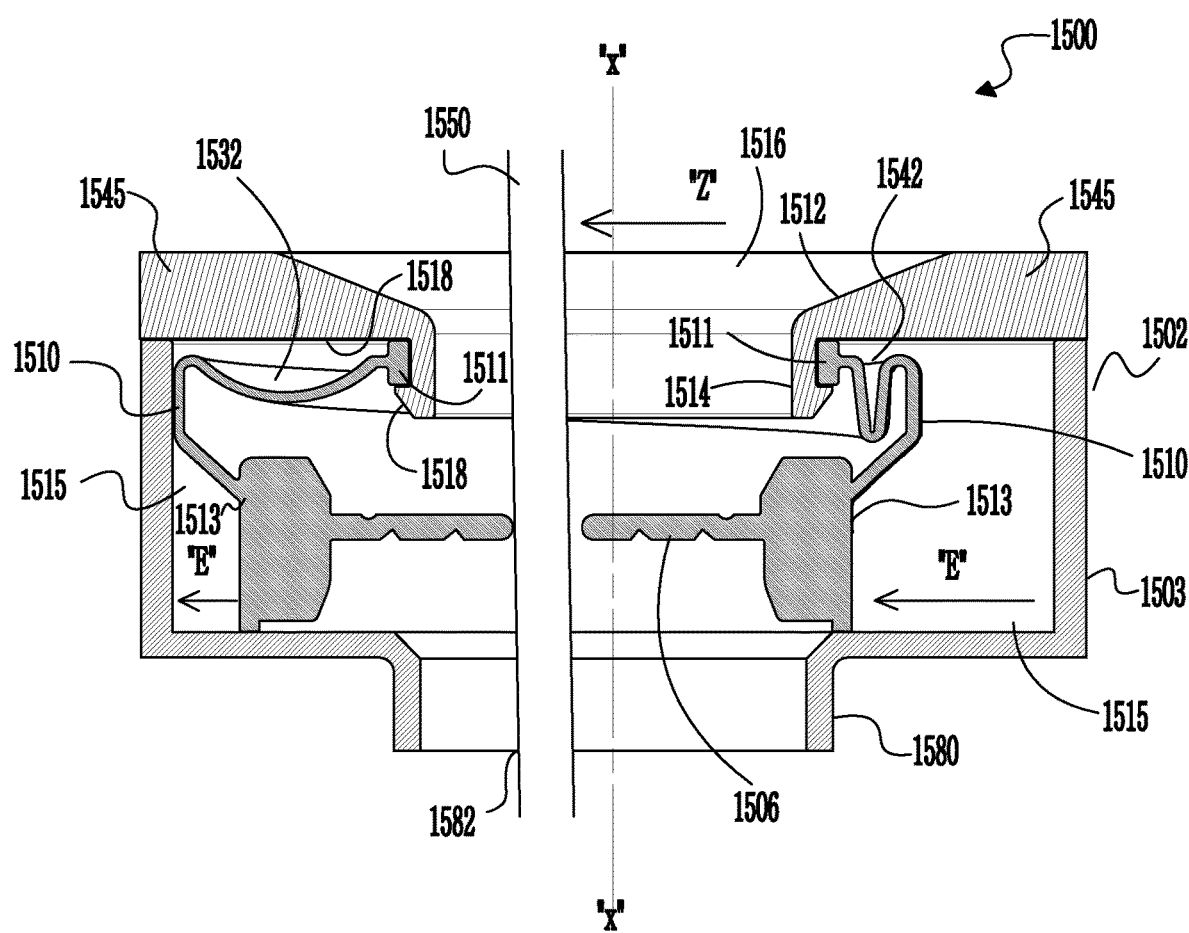
FIGS. 13B and 13C are side views of the flat seal where the bellows is contracted on one end and expanded on the other end when a surgical instrument passes therethrough, where the bellows and the flat seal are one integral unit, in accordance with an embodiment of the present disclosure.
Figure 13C:
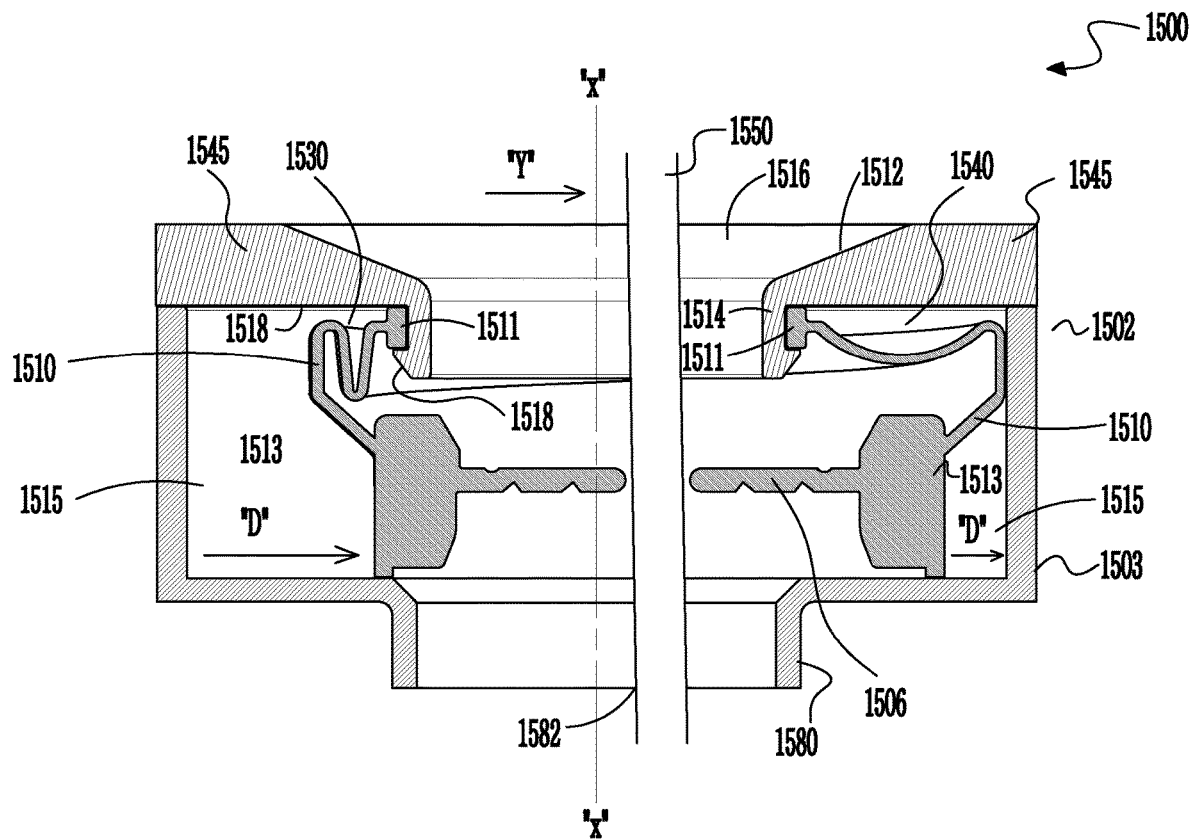

Referring to FIG. 13A, a side view 1500 of a flat seal 1506, where the bellows 1510 and the flat seal 1506 are one integral unit, in accordance with another embodiment of the present disclosure is presented. FIGS. 13B and 13C are side views 1500 of the flat seal 1506 where the bellows 1510 is contracted on one end and expanded on the other end when the surgical instrument 1550 passes therethrough, where the bellows 1510 and the flat seal 1506 are one integral unit, in accordance with an embodiment of the present disclosure.

Cannula housing 1502 is adapted and dimensioned to accommodate seal 1506, which is a flat seal. Seal 1506 is mounted in a manner that permits lateral movement of the seal 1506 relative to seal axis "x." The top portion of the cannula housing 1502 includes angled portions 1512 for enabling angular insertion of the surgical instrument 1550. The angulation allows for easier insertion and manipulation of the surgical instrument 1550. The angled portions 1512 taper off to define an inner guide wall 1514. The inner guide wall 1514 may be a substantially vertical wall that is parallel to axis "x." An outer wall 1518 is defined within a proximal end of annular space 1515. Annular space 1515 includes a bellows 1510 having a proximal end 1511 (or first end) and a distal end 1513 (or second end). The bellows 1510 is confined within the annular space 1515.

A portion of the outer wall 1518 is configured to receive and secure the proximal end 1511 of bellows 1510. The distal end 1513 of the bellows 1510 is configured to be interconnected with the seal 1506 in order to form a single, integral unit. The bellows 1510 acts as a centering unit for maintaining the seal 1506 in a compressed or tensioned position when the surgical instrument 1550 is inserted through opening 1516. It is contemplated that the centering unit 1510 is some type of flexible or semi-rigid rubber structure, similar to the structure of the seal 1506. In FIG. 13A, the bellows 1510 is shown in an un-tensioned or neutral configuration 1533. In other words, insertion of the surgical instrument 1550 does not cause deflection or displacement of the bellows 1510.

As illustrated, the first end 1511 of the bellows 1510 is attached or connected to a proximal wall 1545 of the cannula housing 1502. Thus, bellows 1510 provides some self-centering that pushes or readjusts the seal 1506 toward a centered, un-tensioned position. Therefore, the first end 1511 of the bellows 1510 connects to a top wall or top portion or top segment or distal portion/segment of the cannula housing 1502 (as opposed to the side walls 1503 of the cannula housing 1502). The vertical structure of the bellows 1510 also provides self-centering that pushes the seal 1506 toward a center position with respect to axis "x." Moreover, the width (and overall size of the system) of the cannula housing 1502 may be reduced by constructing the bellows 1510 as a vertical structure that connects to the top wall of the cannula housing 1502 because less space is required on the sides of the cannula housing 1502. Thus, the space between the side walls 1503 of the cannula housing 1502 and the bellows 1510 may be minimized. In other words, the radial width of the cannula housing 1502 may be decreased substantially.

Figure 14A:
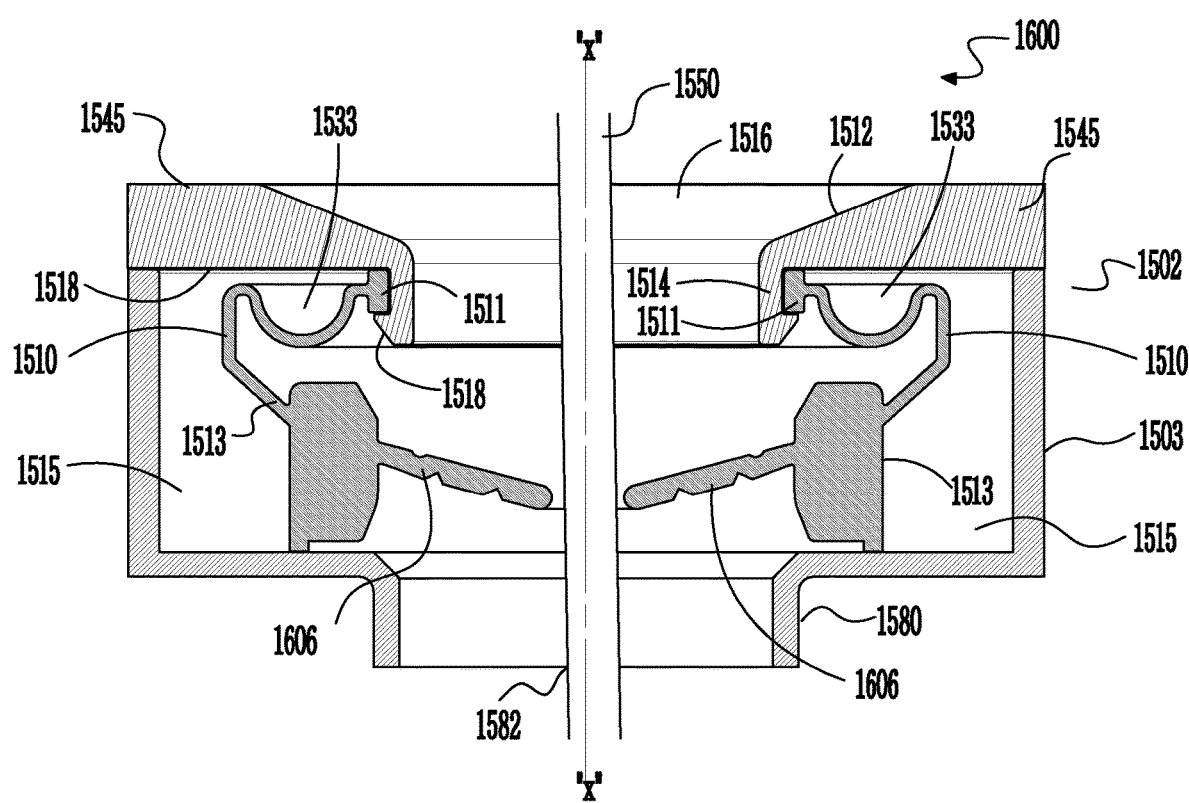
FIG. 14A is a side view of a slightly conical seal, where the bellows and the slightly conical seal are one integral unit, in accordance with another embodiment of the present disclosure.
Figure 14B:
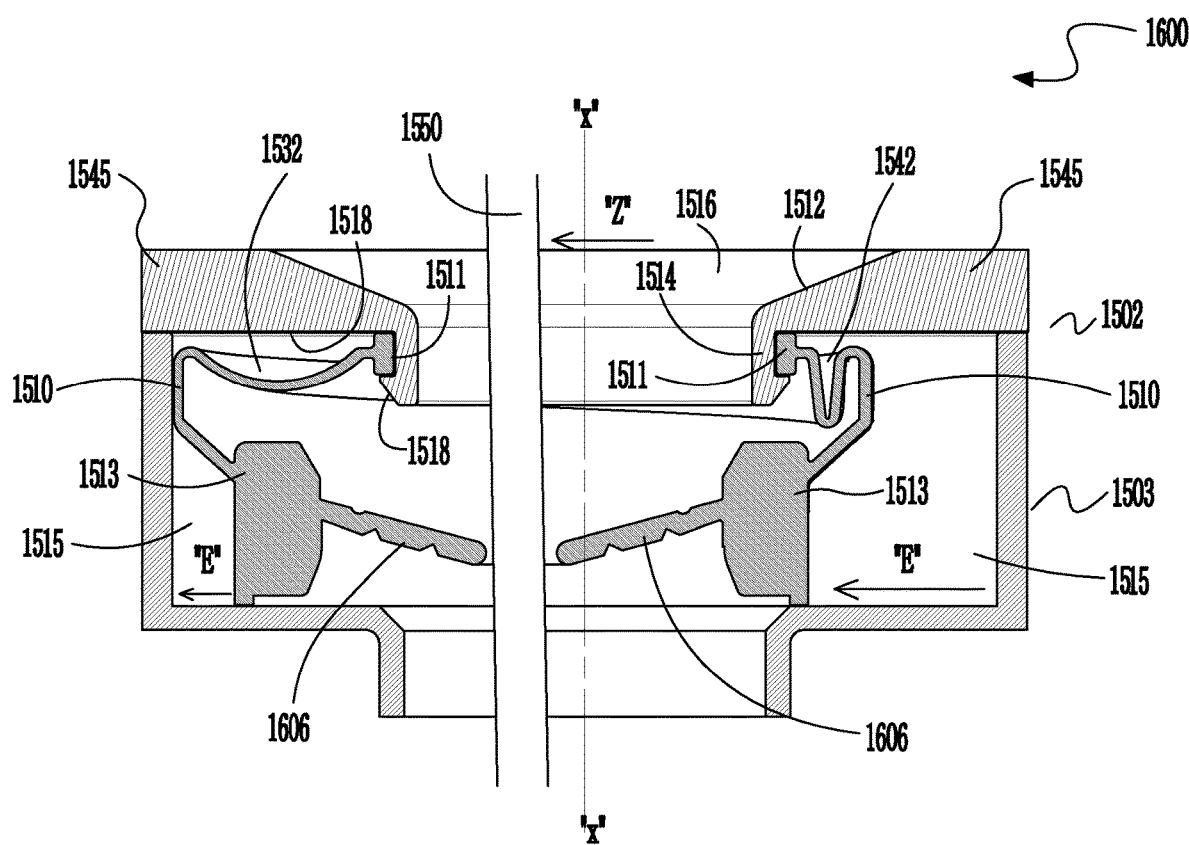
FIGS. 14B and 14C are side views of the slightly conical seal where the bellows is contracted on one end and expanded on the other end when a surgical instrument passes therethrough, where the bellows and the slightly conical seal are one integral unit, in accordance with an embodiment of the present disclosure.
Figure 14C:
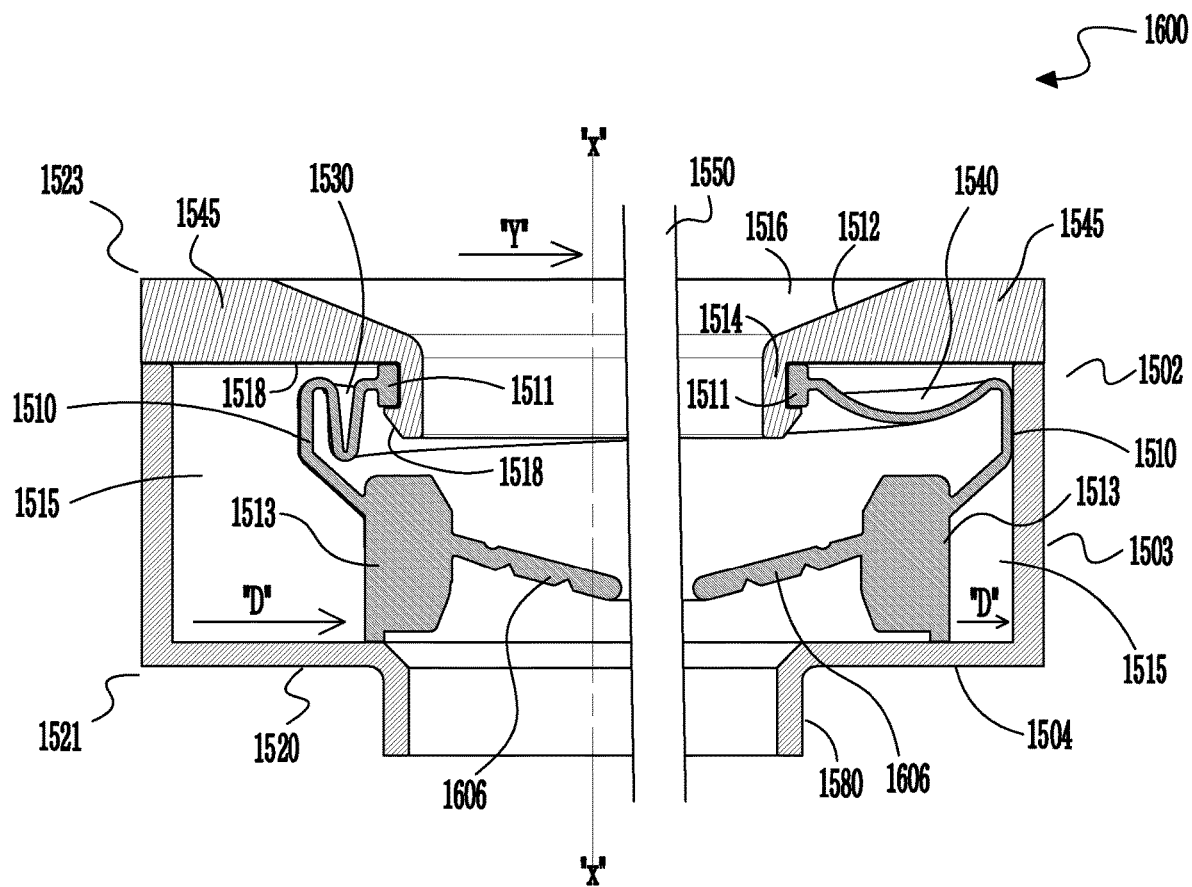
Figure 15A:
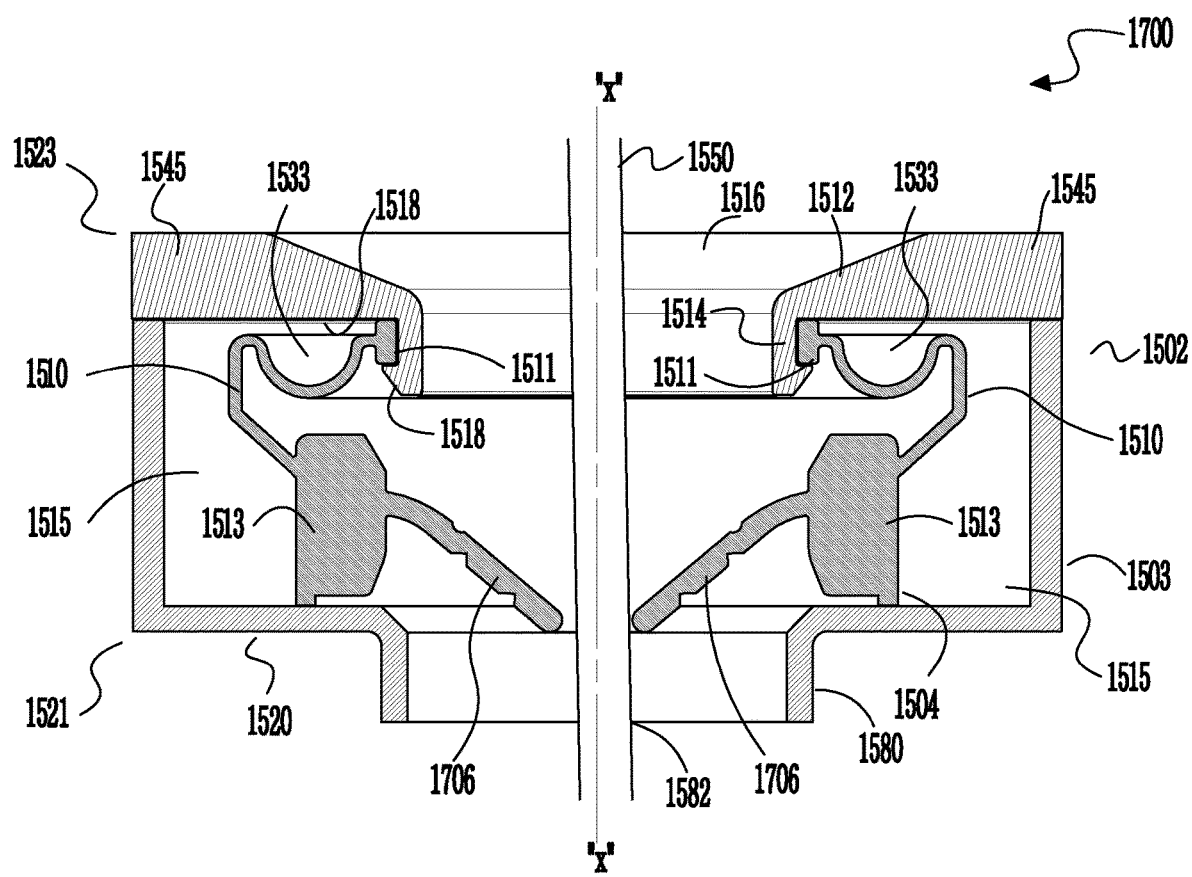
FIG. 15A is a side view of a steep conical seal, where the bellows and the steep conical seal are one integral unit, in accordance with another embodiment of the present disclosure.
Figure 15B:
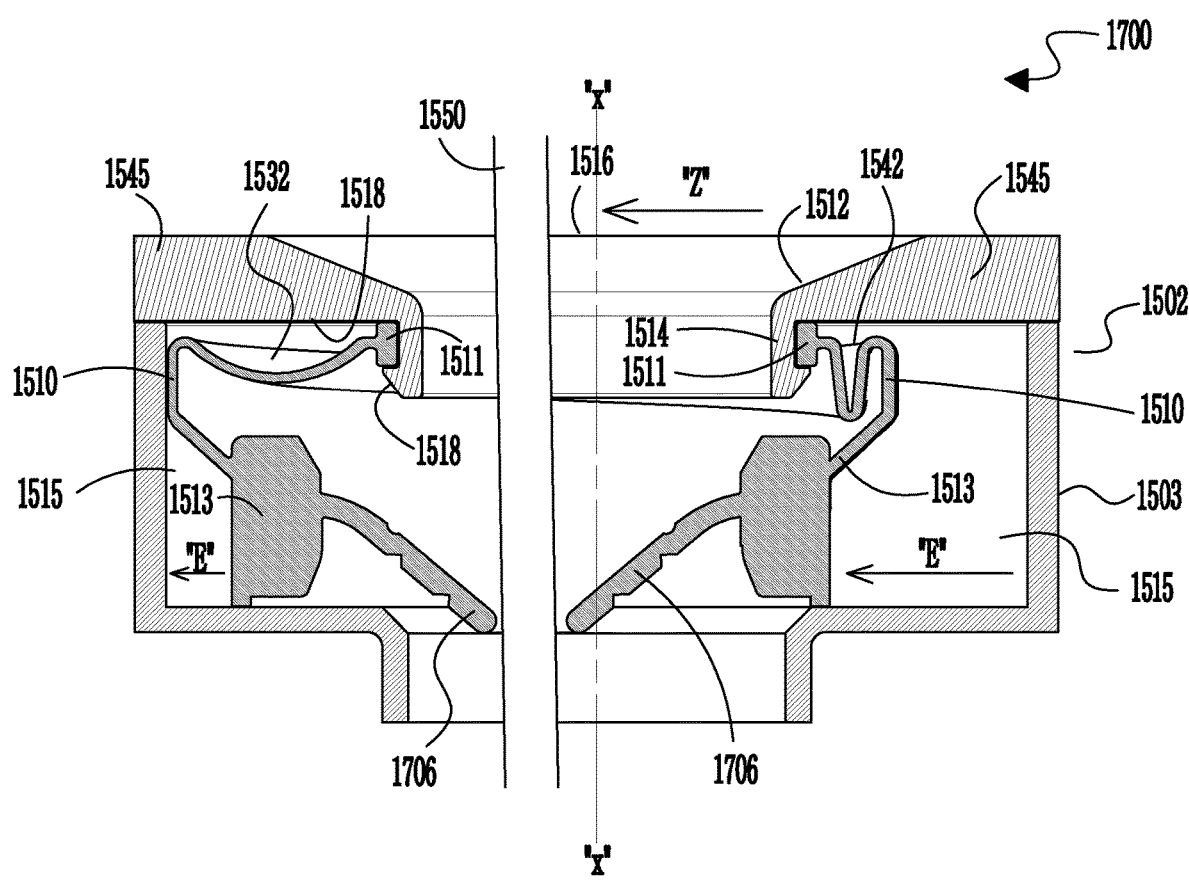
FIGS. 15B and 15C are side views of the steep conical seal where the bellows is contracted on one end and expanded on the other end when a surgical instrument passes therethrough, where the bellows and the steep conical seal are one integral unit, in accordance with an embodiment of the present disclosure.
Figure 15C:
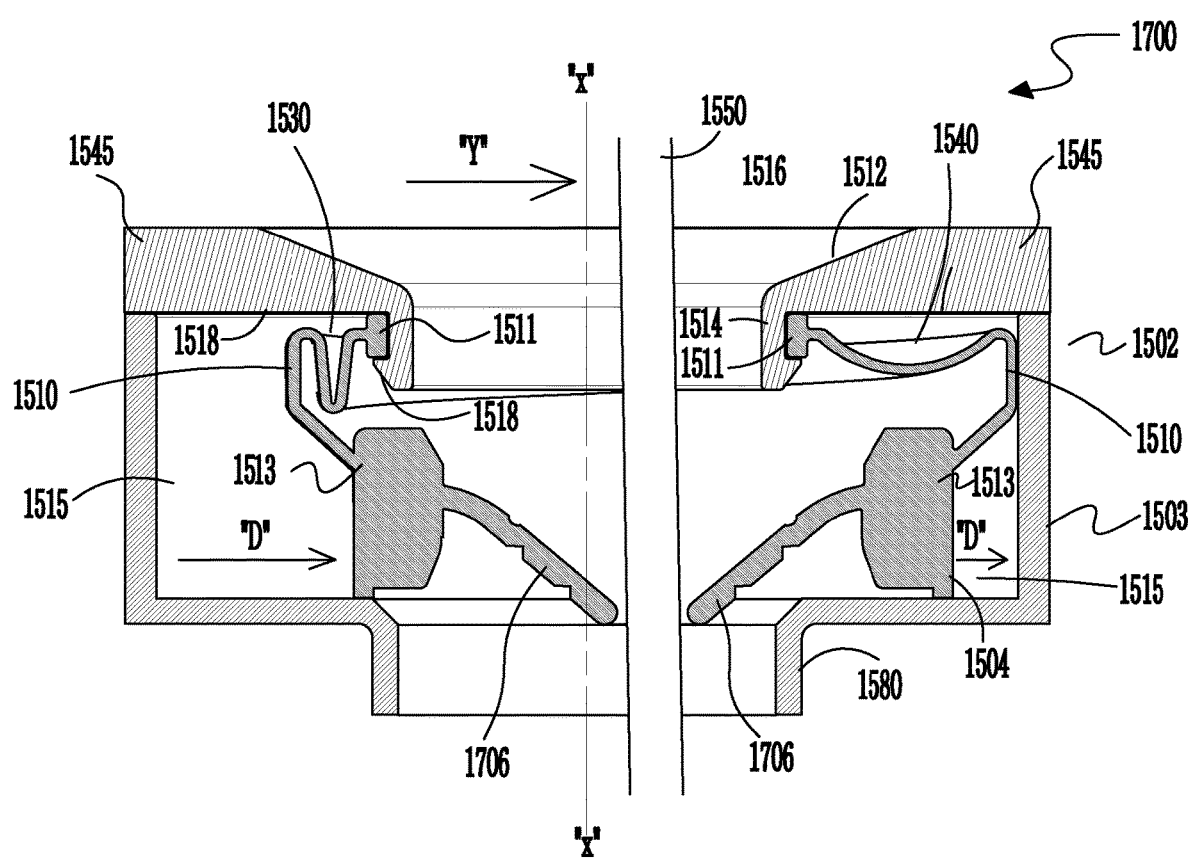

FIGS. 14A-14C illustrate the same structure as FIGS. 13A-13C, with one main difference. Instead of a flat seal 1506, a slightly conical seal 1606 is depicted. Additionally, FIGS. 15A-15C illustrate the same structure as FIGS. 13A-13C, with one main difference. Instead of a flat seal 1506, a steeply conical seal 1706 is depicted. The seals 1606 and 1706 function similarly to the seal 1506, described above. Thus, for sake of clarity, a detailed description of FIGS. 14A-15C will be omitted.

Therefore, in summary, the use of a bellows provides an additional sealing benefit, as insufflation gas is inhibited by the bellows from escaping between the seal and the cannula housing. Attaching the bellows to the proximal wall of the cannula housing also decreases or eliminates the need for additional spacing within the cannula housing in a location proximal to the seal, thereby enabling the height and width of the cannula housing to be reduced. Still further, the bellows provides a relatively small amount of biasing force to the seal—such a small force may be advantageous when a surgeon is using the device. More specifically, the bellows provides for a biasing force that is large enough to enable the benefits of self-centering the laterally moving seal, but small enough such that manipulation of an instrument within the cannula housing won't cause the passage of the seal to become "cat-eyed" or stretched to a degree that would cause leakage.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A seal assembly comprising:
   an outer housing defining a central longitudinal axis and having a longitudinal passage for receiving at least one surgical object therethrough;

an inner housing movably disposed within the outer housing;

a seal cooperating with the inner housing; and a bellows having a first end engaging the outer housing and a second end engaging the inner housing, the second end of the bellows being longitudinally spaced distally of the first end of the bellows, wherein the bellows is dimensioned and adapted to establish a biasing relationship with the inner housing.

2. The seal assembly of claim 1, further including a cannula sleeve extending from the outer housing.

3. The seal assembly of claim 1, wherein the inner housing is adapted for lateral movement relative to the central longitudinal axis of the outer housing.

4. The seal assembly of claim 1, wherein the bellows is configured to overcome any friction between the outer housing and the inner housing to permit the seal to align with the central longitudinal axis of the outer housing.

5. The seal assembly of claim 1, wherein the bellows is circumferentially adjacent the longitudinal passage of the outer housing.

6. The seal assembly of claim 1, wherein the outer housing defines an angular opening therethrough to facilitate angular reception of the at least one surgical object.

7. The seal assembly of claim 1, wherein the bellows is dimensioned and adapted to prevent passage of fluids through the outer housing.

8. The seal assembly of claim 1, wherein the bellows enables self-centering of the seal after the at least one surgical object has been removed from the longitudinal passage.

9. The seal assembly of claim 1, wherein the bellows extends to a proximal wall of the outer housing in parallel to the central longitudinal axis defined by the outer housing.

10. The seal assembly of claim 1, wherein the bellows is integrally formed with the inner housing and the seal.

11. A seal assembly comprising:

an outer housing defining a central longitudinal axis and having a longitudinal passage for receiving at least one surgical object therethrough, the outer housing defining an angular opening therethrough to facilitate angular reception of the at least one surgical object;

an inner housing movably disposed within the outer housing;

a seal cooperating with the inner housing; and a bellows having a first end engaging the outer housing and a second end engaging the inner housing, the second end of the bellows being longitudinally spaced distally of the first end of the bellows.

12. The seal assembly of claim 11, further including a cannula sleeve extending from the outer housing.

13. The seal assembly of claim 11, wherein the bellows is dimensioned and adapted to establish a biasing relationship with the inner housing.

14. The seal assembly of claim 11, wherein the inner housing is adapted for lateral movement relative to the central longitudinal axis of the outer housing.

15. The seal assembly of claim 11, wherein the bellows is configured to overcome any friction between the outer housing and the inner housing to permit the seal to align with the central longitudinal axis of the outer housing.

16. The seal assembly of claim 11, wherein the bellows is circumferentially adjacent the longitudinal passage of the outer housing.

17. The seal assembly of claim 11, wherein the bellows is dimensioned and adapted to prevent passage of fluids through the outer housing.

18. The seal assembly of claim 11, wherein the bellows enables self-centering of the seal after the at least one surgical object has been removed from the longitudinal passage.

19. The seal assembly of claim 11, wherein the bellows extends to a proximal wall of the outer housing in parallel to the central longitudinal axis defined by the outer housing.

20. The seal assembly of claim 11, wherein the bellows is integrally formed with the inner housing and the seal.

\* \* \* \* \*